United States Patent
Rubey et al.

(10) Patent No.: US 11,684,246 B2
(45) Date of Patent: Jun. 27, 2023

(54) INFLATABLE IN-VIVO CAPSULE ENDOSCOPE WITH MAGNETIC GUIDE

(71) Applicant: AnX Robotica Corp., Plano, TX (US)

(72) Inventors: Kevin Rubey, Ventura, CA (US); Xiaodong Duan, Pleasanton, CA (US)

(73) Assignee: AnX Robotica Corp., Plano, TX (US)

( * ) Notice: Subject to any disclaimer, the term of this patent is extended or adjusted under 35 U.S.C. 154(b) by 41 days.

(21) Appl. No.: 17/382,730

(22) Filed: Jul. 22, 2021

(65) Prior Publication Data

US 2021/0345863 A1  Nov. 11, 2021

Related U.S. Application Data

(63) Continuation of application No. 17/062,124, filed on Oct. 2, 2020, now Pat. No. 11,089,946.

(60) Provisional application No. 62/911,688, filed on Oct. 7, 2019.

(51) Int. Cl.
*A61B 1/00* (2006.01)
*A61B 1/04* (2006.01)

(52) U.S. Cl.
CPC ...... *A61B 1/00158* (2013.01); *A61B 1/00082* (2013.01); *A61B 1/041* (2013.01)

(58) Field of Classification Search
CPC .. A61B 1/00082; A61B 1/00158; A61B 1/041
See application file for complete search history.

(56) References Cited

U.S. PATENT DOCUMENTS

| | | | |
|---|---|---|---|
| 9,986,898 B2 | 6/2018 | Duan et al. |
| 9,999,415 B2 | 6/2018 | Duan et al. |
| 10,076,234 B2 | 9/2018 | Duan et al. |
| 10,314,514 B2 | 6/2019 | Duan |
| 10,478,047 B2 | 11/2019 | Duan et al. |
| 10,500,127 B2 | 12/2019 | Duan et al. |
| 10,517,466 B2 | 12/2019 | Ye et al. |
| 2003/0018280 A1 | 1/2003 | Lewkowicz et al. |
| 2006/0155163 A1 | 7/2006 | Yachia et al. |
| 2007/0010709 A1 | 1/2007 | Reinschke |
| 2007/0161851 A1 | 7/2007 | Takizawa et al. |
| 2007/0221233 A1 | 9/2007 | Kawano et al. |

(Continued)

*Primary Examiner* — Aaron B Fairchild
(74) *Attorney, Agent, or Firm* — Pearl Cohen Zedek Latzer Baratz LLP

(57) ABSTRACT

An inflatable in-vivo capsule endoscope and method of operation is provided. The inflatable in-vivo capsule endoscope may include a sensing device for capturing in-vivo images and one or more permanent magnets for magnetically guiding the endoscope, housed interior to a capsule-shaped body. The inflatable in-vivo capsule endoscope may include an inflatable buoy attached externally to the capsule-shaped body. An inflation device may inflate the in-vivo capsule endoscope to reduce its specific gravity by injecting gas into the inflatable buoy, such that when the inflatable buoy is injected with an above threshold volume of gas, the inflatable in-vivo capsule endoscope floats in liquid. The inflatable in-vivo capsule endoscope may be magnetically guided via its permanent magnets when exposed to an externally generated magnetic field. A reduced magnetic field strength and external magnet size may be used to magnetically navigate an inflated capsule floating in liquid than a conventional uninflated capsule.

8 Claims, 44 Drawing Sheets

Capsule endoscope device for spiral advancement

(56) References Cited

U.S. PATENT DOCUMENTS

| | | | |
|---|---|---|---|
| 2008/0015413 A1* | 1/2008 | Barlow | A61B 1/00147 |
| | | | 600/114 |
| 2008/0207999 A1 | 8/2008 | Abraham-Fuchs et al. | |
| 2009/0281387 A1 | 11/2009 | Takizawa et al. | |
| 2010/0001592 A1 | 1/2010 | Kawano et al. | |
| 2011/0060189 A1 | 3/2011 | Belson | |
| 2013/0184526 A1 | 7/2013 | Takizawa et al. | |
| 2013/0267788 A1 | 10/2013 | Duan et al. | |
| 2014/0187907 A1 | 7/2014 | Duan et al. | |
| 2014/0247039 A1 | 9/2014 | Duan et al. | |
| 2015/0011829 A1 | 1/2015 | Wang et al. | |
| 2015/0380140 A1 | 12/2015 | Duan et al. | |
| 2016/0270639 A1 | 9/2016 | Trollsas et al. | |
| 2016/0310357 A1 | 10/2016 | Duan et al. | |
| 2017/0020374 A1 | 1/2017 | Duan et al. | |
| 2017/0035520 A1 | 2/2017 | Duan et al. | |
| 2017/0296428 A1 | 10/2017 | Duan et al. | |
| 2018/0084976 A1 | 3/2018 | Duan et al. | |
| 2020/0323422 A1 | 10/2020 | Duan | |

\* cited by examiner

Capsule endoscope attached to the inner surface of the balloon with adhesive

As the bladder inflates after air injection, the assembly size changes and the overall density changes, forming different orientations such as sinking to the bottom, suspending in the liquid and floating on the liquid.

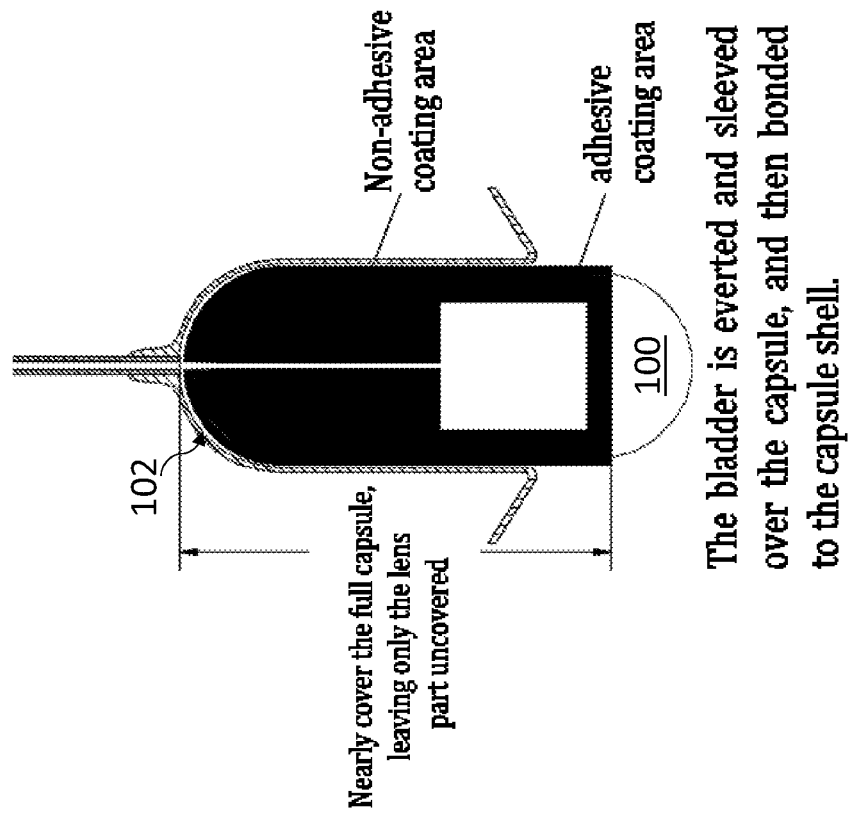
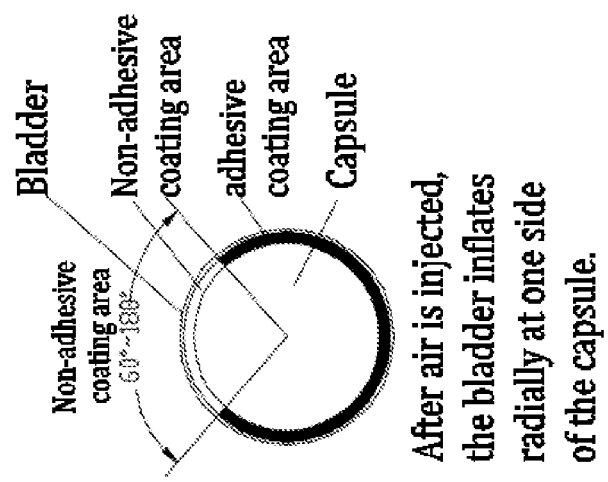
Fig. 17

Inflatable and deflatable balloon with external thread

Capsule endoscope device for spiral advancement

Fig. 23 — Capsule endoscope device for spiral advancement in small intestine

The elastic bladder is made of elastomer film, with a thickness of 0.1 to 0.5 mm. The inner diameter of the bladder is equal to the outer diameter of the capsule endoscope. After assembly, the capsule size is almost unchanged, and so, it will not affect swallowing.

The gas generation unit turns when capsule gets into the small bowl. The spiral structure may proper the capsule forward or backward depends on the clockwise or anticlockwise rotation of the capsule around its long axis.

The elastic member on the capsule surface can be inflated by the gas generated in the capsule. The inflated balloon can help to float the capsule in the water that help to control the magnetic capsule endoscope inside the stomach. When the balloon is large enough, the capsule can stay inside the stomach as the observation device for the lesions or blooding of stomach.

Fig. 32

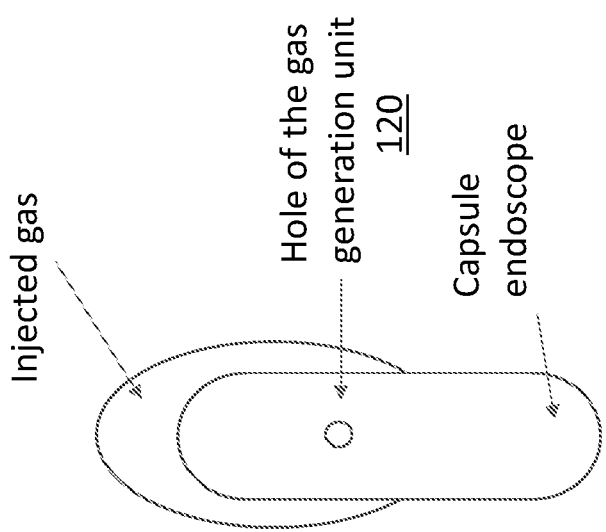

Put an annular bladder on a dual-camera capsule endoscope and bond them together with adhesive to constitute a capsule assembly. The inside of the bladder forms a closed cavity. Inflate or deflate the bladder through an air injection tube to change the volume of the capsule assembly.

Form of the capsule assembly after the bladder is inflated.

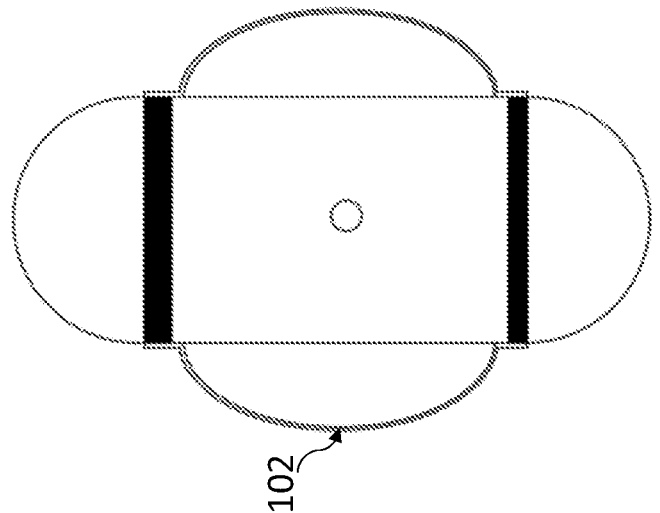
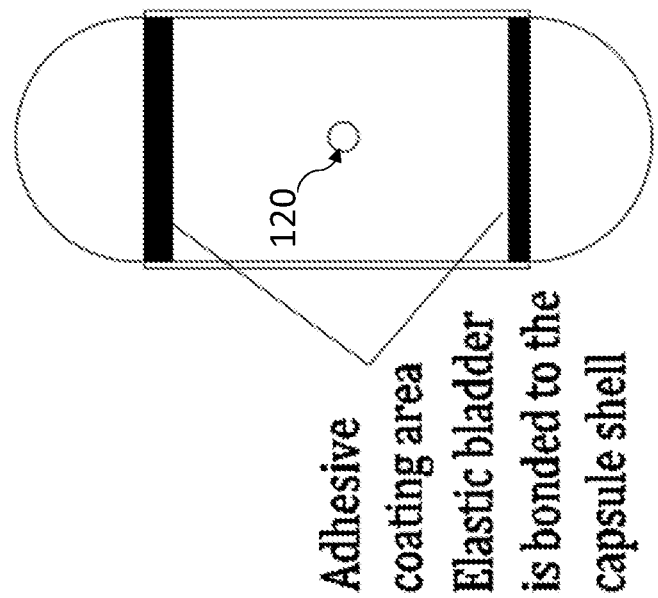
Fig. 41

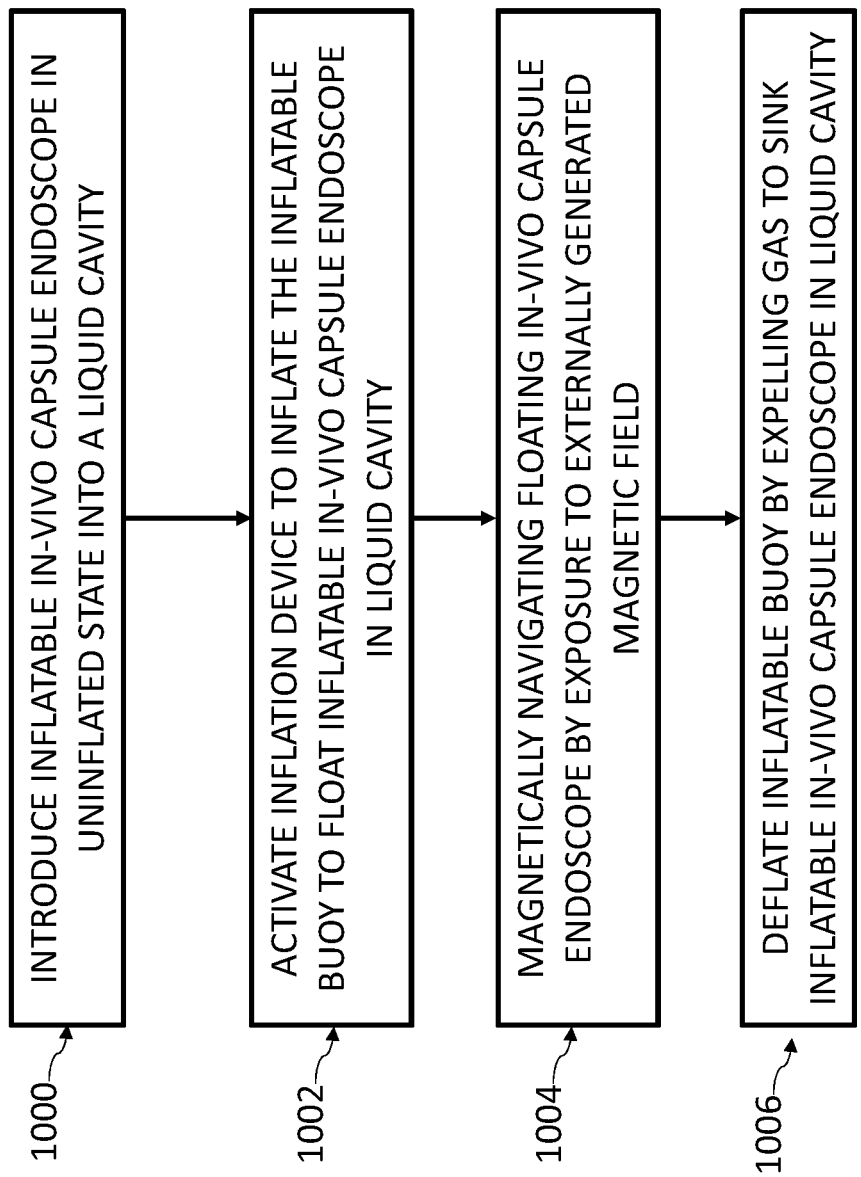

INFLATABLE IN-VIVO CAPSULE ENDOSCOPE WITH MAGNETIC GUIDE

CROSS-REFERENCE TO RELATED APPLICATIONS

This application is a continuation of U.S. patent application Ser. No. 17/062,124 filed Oct. 2, 2020, which in turn claims the benefit of U.S. Provisional Application Ser. No. 62/911,688, filed Oct. 7, 2019, both of which are hereby incorporated by reference in their entirety.

FIELD OF THE INVENTION

Embodiments of the invention relate to an ingestible or in-vivo capsule endoscope configured to traverse and image at least a portion of the gastro-intestinal (GI) tract. More particularly, some embodiments relate to an ingestible capsule endoscope that has a permanent magnetic dipole moment configured to be magnetically guided while inside a human by a magnetic field generated by a magnetic device positioned external to the human body.

BACKGROUND OF THE INVENTION

Conventional in-vivo capsule endoscopes are guided magnetically to move through the human body. These capsules contain magnets, batteries, cameras, and other electronics that are relatively heavier than, and thus sink in, liquid. So, when the capsule passes into a liquid-filled cavity, such as the stomach, the capsule generally sinks to the bottom of the cavity.

Once sunk, the capsule rests on the cavity floor, and needs a relatively strong magnetic force, e.g., 0.006 Newtons (N)-0.06N, to overcome forces of friction and drag between the capsule and the cavity floor in order to be moved. Generally, conventional systems require a large bed of magnets to create a magnetic field strong enough to magnetically turn or move the sunken capsule. Such magnets typically occupy an entire room and are not meant to be moved, limiting access and portability to those in need. Additionally, when the capsule sinks, its field of view is generally obstructed by the cavity walls and floor, blocking objects of interest in images captured by the capsule.

Accordingly, there is a need in the art for a more efficient system to magnetically guide in-vivo capsule endoscopes.

SUMMARY OF EMBODIMENTS OF THE INVENTION

To solve the aforementioned problems in the art, embodiments of the invention provide an inflatable in-vivo capsule endoscope system that causes the capsule to float in liquid. When floating, the capsule is suspended in liquid above the floor of the stomach or other liquid-filled cavity. This buoyancy makes the capsule significantly easier to move magnetically by reducing forces of friction or drag e.g., between the capsule and the cavity walls. A floating capsule requires a significantly weaker magnetic force, e.g., 0.0006 Newtons (N)-0.006N, to guide the capsule than does a sunken capsule (e.g., a ten-fold or order of magnitude reduction). Such a magnetic field can be generated by a smaller magnet than in conventional systems. In some embodiments, the magnet may be small enough to be handheld or portable, making magnetically guided capsule endoscopy accessible to a wider range of patients.

Additionally, because a floating capsule is spaced from the cavity floor, embodiments of the invention may reduce or eliminate obstructions or occlusions by the cavity walls or floor to the capsule imager's field of view. Accordingly, embodiments of the invention may improve the visibility of objects of interest in images generated by the floating capsule endoscope, as compared to a conventional sunken capsule endoscope. In some embodiments, the level of inflation may be adjusted or tuned, such that, the capsule may float to a height below the liquid surface to prevent refraction or glare at the surface to further improve image quality.

In an embodiment of the invention, an inflatable in-vivo capsule endoscope is provided comprising a capsule-shaped body, a sensing device for capturing in-vivo images housed interior to the capsule-shaped body, an inflatable buoy external to the capsule-shaped body, and one or more permanent magnets housed interior to the capsule-shaped body. An inflation device may be configured to inflate the in-vivo capsule endoscope by injecting gas into the inflatable buoy to reduce the specific gravity of the in-vivo capsule endoscope. When the inflatable buoy is injected with an above threshold volume of gas, the inflatable in-vivo capsule endoscope is configured to float in liquid. The one or more permanent magnets have a permanent magnetic moment for magnetically guiding the inflatable in-vivo capsule endoscope when exposed to an externally generated magnetic field.

In an embodiment of the invention, a method of operating an inflatable in-vivo capsule endoscope is provided. An inflatable in-vivo capsule endoscope may be introduced in an uninflated state into a cavity comprising liquid inside an organism. The capsule endoscope may comprise a capsule-shaped body, an inflatable buoy external to the capsule-shaped body, and a sensing device for capturing in-vivo images housed interior to the capsule-shaped body. An inflation device may be activated to inflate the inflatable buoy by injecting an above threshold volume of gas into the inflatable buoy to reduce the specific gravity of the in-vivo capsule endoscope, such that, the inflatable in-vivo capsule endoscope floats in the liquid cavity. The floating in-vivo capsule endoscope may be magnetically navigated by exposing one or more permanent magnets housed interior to the capsule-shaped body having a permanent magnetic dipole moment to an externally generated magnetic field that magnetically guides the inflatable in-vivo capsule endoscope.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 17-18 are schematic illustrations of a radially and longitudinally asymmetric inflation buoy, according to an embodiment of the invention;

FIG. 32 is a schematic illustration of an autonomous capsule endoscope comprising a hole for transporting gas from an internal inflation device to an external inflation buoy, according to an embodiment of the invention;

FIGS. 40-41 are schematic illustrations of the autonomous bi-directional in-vivo capsule endoscope that is inflatable by a "cup expansion" type buoy, according to an embodiment of the invention;

FIG. 44 is a flowchart of a method of operating an inflatable in-vivo capsule endoscope, according to an embodiment of the invention.

Figure 1:
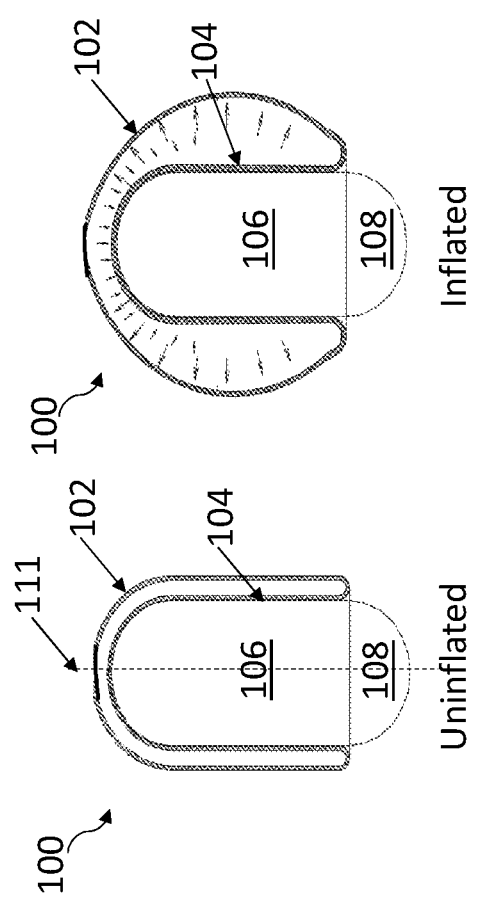
FIG. 1 is a schematic illustration of an inflatable in-vivo capsule endoscope, in an uninflated state (left image) and an inflated state (right image), according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

Reference is made to FIG. 1, which schematically illustrates an inflatable in-vivo capsule endoscope 100 in an uninflated state (left image) and an inflated state (right image), according to an embodiment of the invention. Inflatable in-vivo capsule endoscope 100 may have a capsule-shaped body 104 and an inflatable buoy 102, externally attached to capsule-shaped body 104. Inflatable buoy 102 is a floatation device, which when inflated by an inflation device (e.g., inflation device surface 112 of FIG. 6) injecting an above threshold volume or pressure of gas into a bladder of the inflatable buoy 102, reduces the capsule's overall density (or specific gravity with respect to water), such that, inflated capsule 100 floats in liquid.

Figure 4:
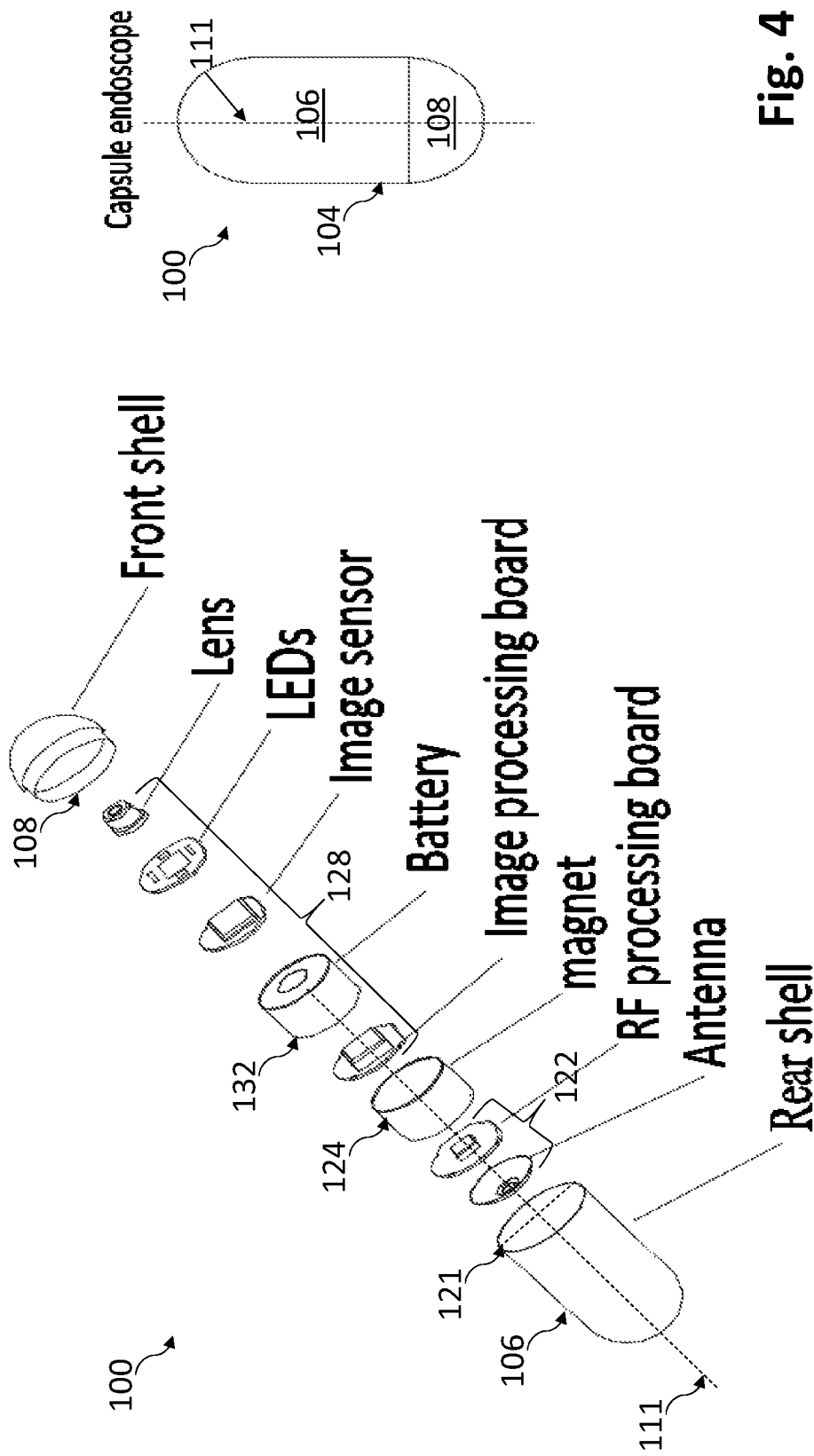
FIG. 4 is a schematic illustration of an exploded view of an inflatable in-vivo capsule endoscope and components thereof, according to an embodiment of the invention.
Figure 5:
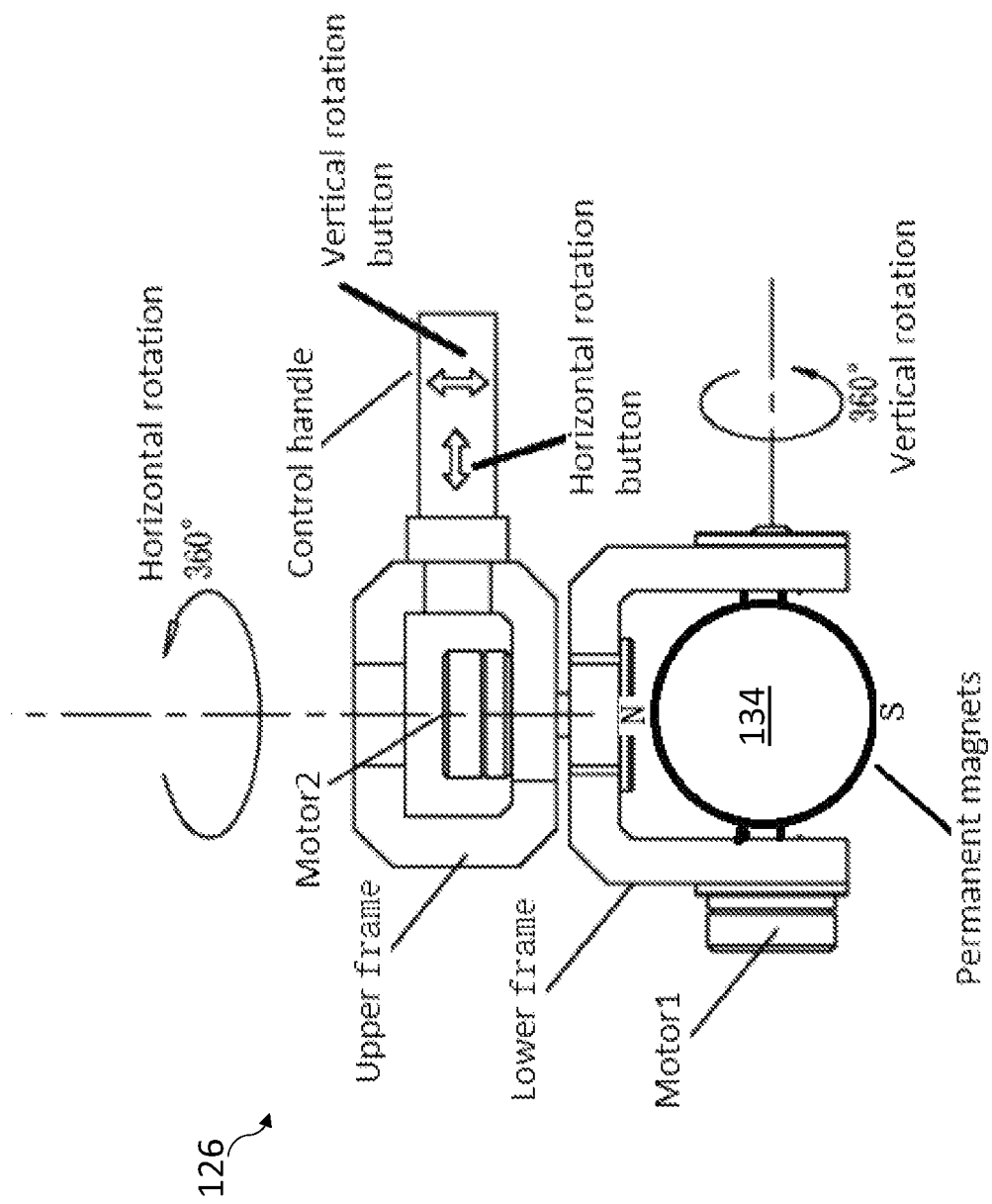
FIG. 5 is a schematic illustration of an external magnetic control system, according to an embodiment of the invention.

Capsule 100 may also have one or more permanent magnets 124 (e.g., as shown in FIG. 4) housed interior to the capsule-shaped body 104 having a permanent magnetic dipole moment. Permanent magnets 124 allow capsule endoscope 100 to be magnetically guided when exposed to a magnetic field generated by an external magnet control system 126 (e.g., as shown in FIG. 5).

Figure 2:
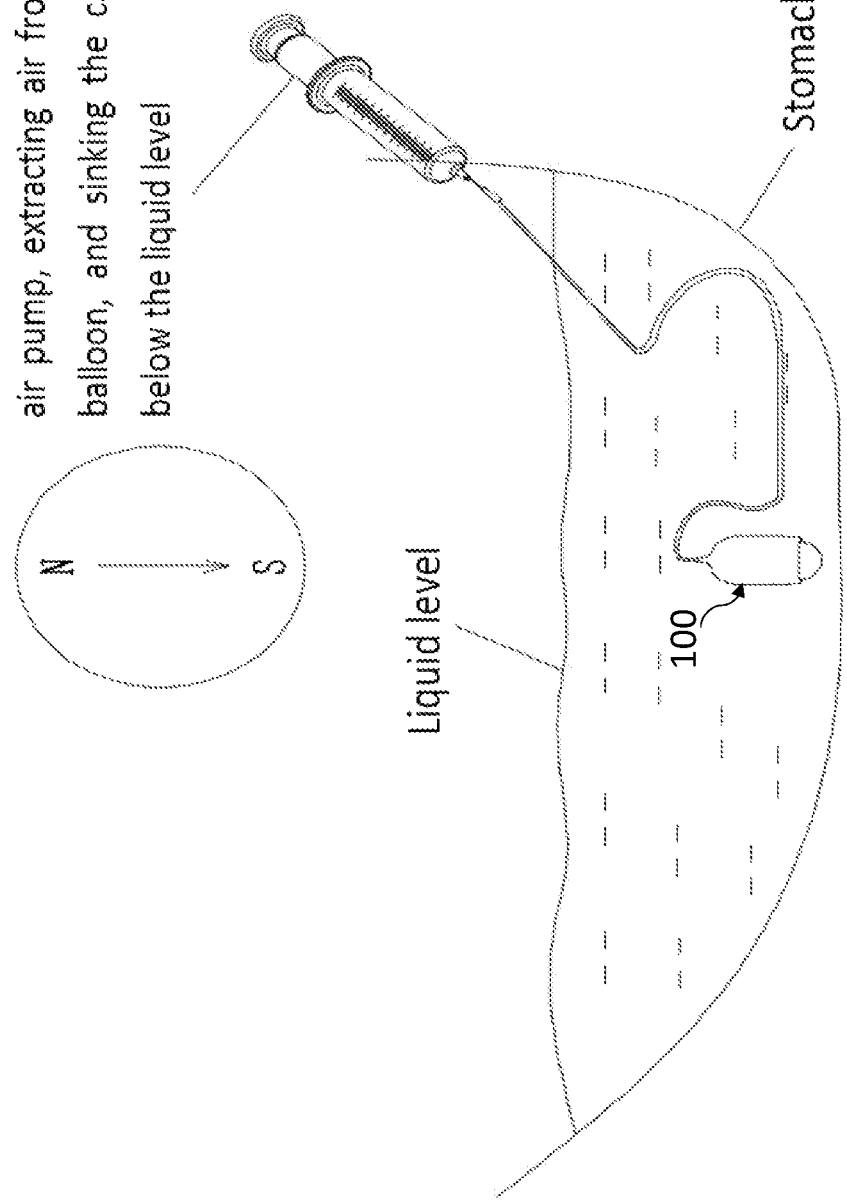
FIGS. 2 and 3 are schematic illustrations of an inflatable in-vivo capsule endoscope in a cavity of an organism in an uninflated state (FIG. 2) and an inflated state (FIG. 3), according to an embodiment of the invention.
Figure 3:
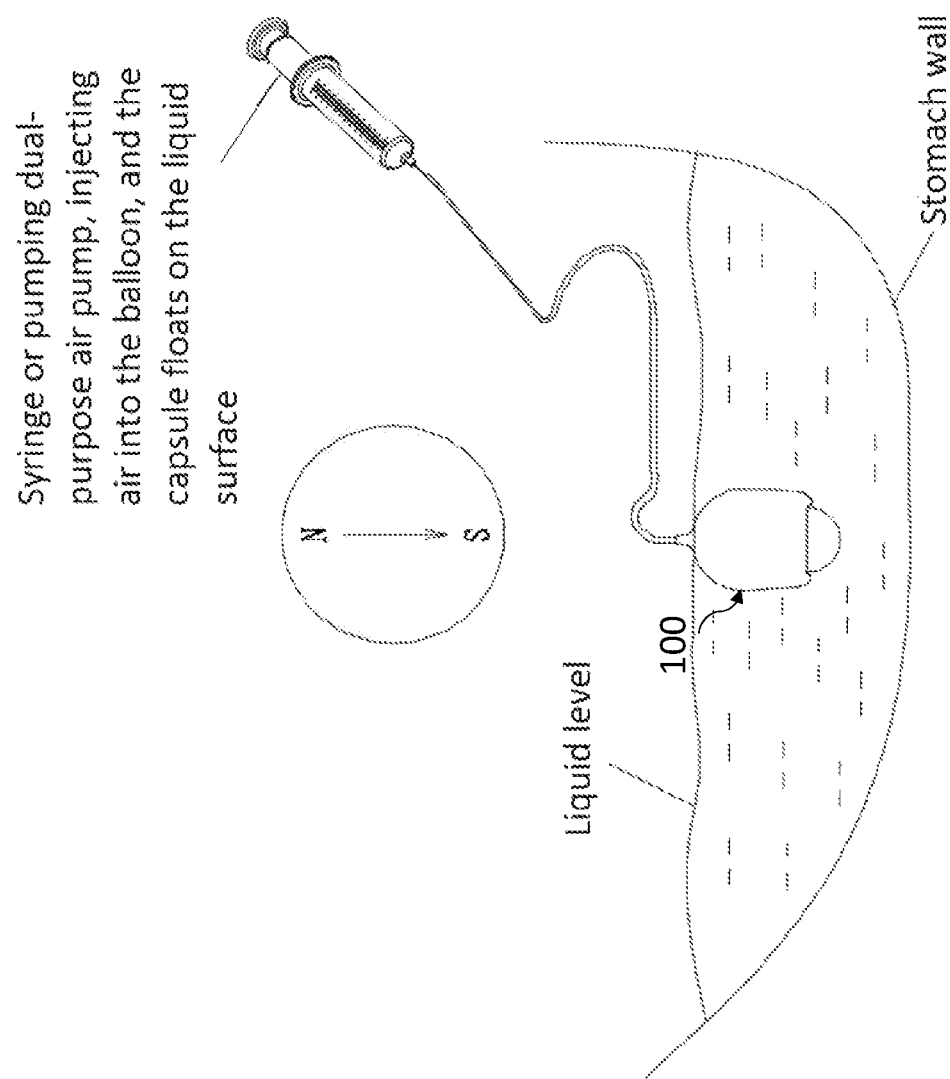

Reference is made to FIGS. 2 and 3, which schematically illustrate inflatable in-vivo capsule endoscope 100 in a cavity of an organism in an uninflated state (FIG. 2) and in an inflated state (FIG. 3), according to an embodiment of the invention. Inflation lifts capsule endoscope 100 from a sunken state, in which it contacts (has substantially zero or negligible distance from) the cavity walls or floor in FIG. 2, to a floating state, in which it is spaced (at a non-zero or relatively greater distance) from the cavity floor in FIG. 3. In some embodiments, inflated capsule 100 may float based solely on the buoyant lift force generated by inflating buoy 102 (e.g., by reducing its density to be less than or equal to the density of water, or reducing its specific gravity with respect to water to be less than or equal to 1). In other embodiments, inflated capsule 100 may float based on a combination of the buoyant lift force (e.g., caused by a reduced capsule density, though still greater than water density) and a magnetic lift force, which together counteract the gravitational sinking force. Buoy 102 may be inflated with gas, such as air, carbon dioxide, nitrogen, or other substances such as foam, oil, or other gaseous or liquid substances or mixtures that have a lower density than water.

In some embodiments, capsule endoscope 100 may be connected to a deflation device (the same "dual-purpose" inflation-deflation device 112 or a different device) configured to deflate buoy 102 by expelling a volume or pressure of gas therefrom. Deflation device may thus increase the density or specific gravity of the in-vivo capsule endoscope so that the inflatable in-vivo capsule endoscope 100 sinks in liquid. In some embodiments, the capsule 100 may expelling a volume of gas to sink to the cavity floor or float at a predefined height below the liquid surface. In some embodiments, the capsule 100 may be sunk solely by deflating the device, or in combination with magnetic forces. In one example, the deflation device may increase the capsule 100 density to be greater than the density of water, or increase its specific gravity with respect to water to be greater than 1. In one embodiment, gas may be expelled by opening a (resealable or non-resealable) hole in the buoy, such that no separate device is used.

Figure 16:
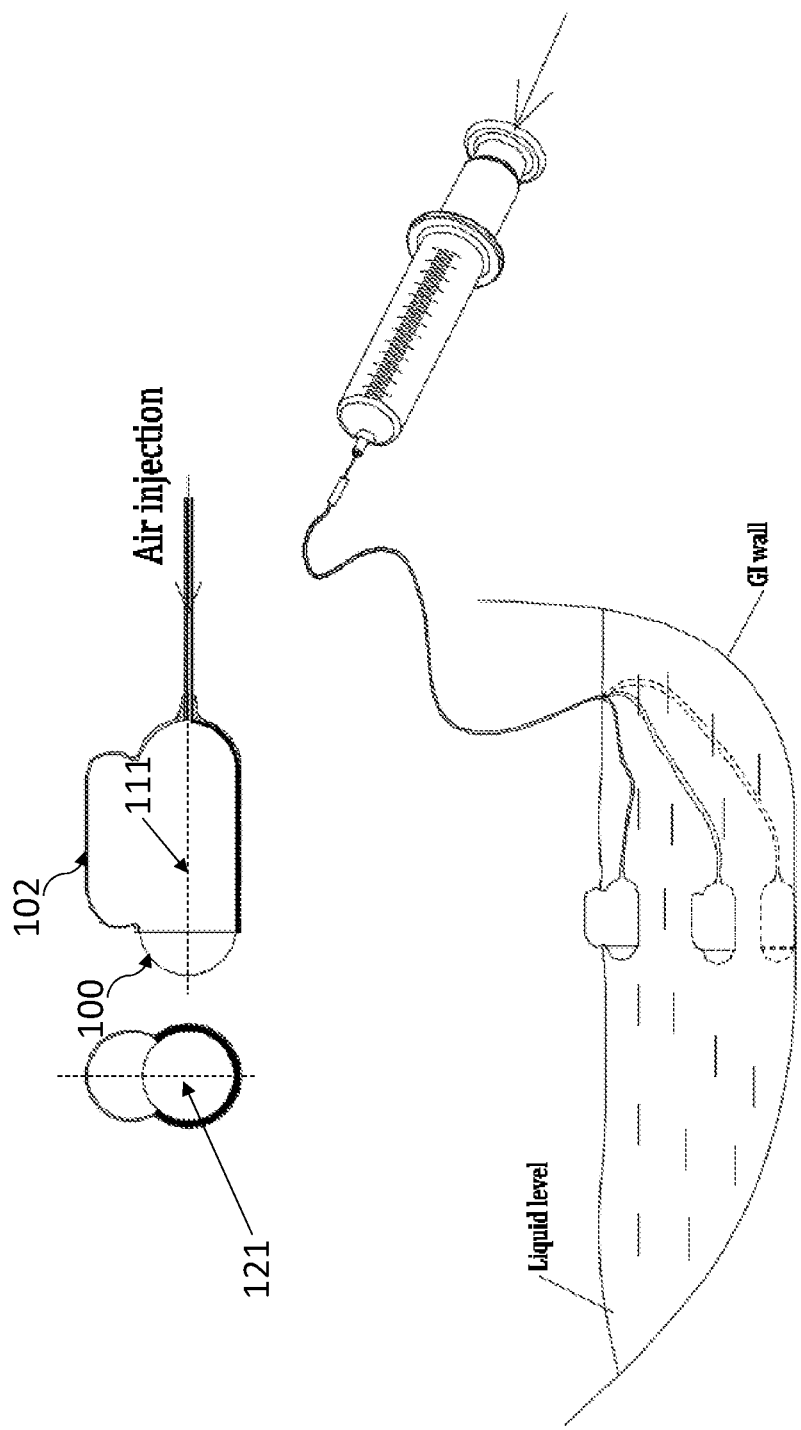
Figure 18:
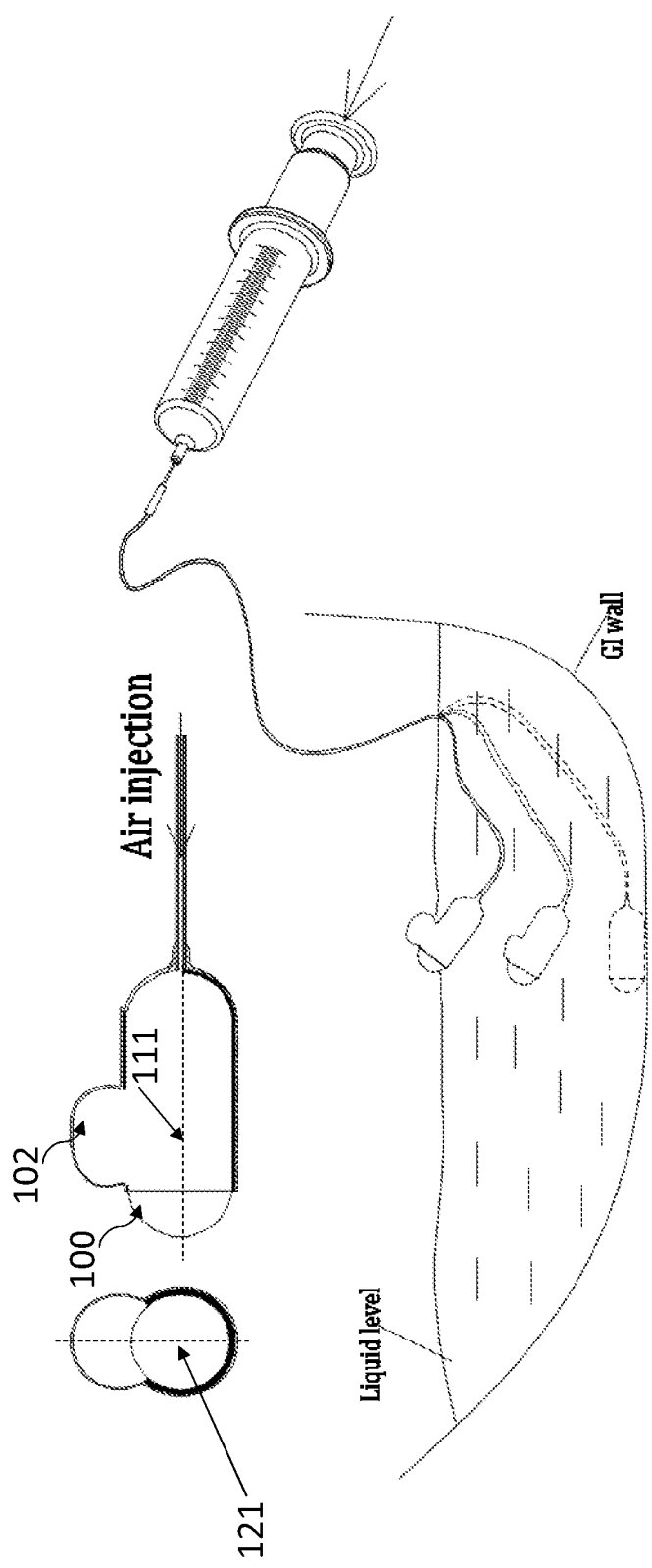
Figure 19:
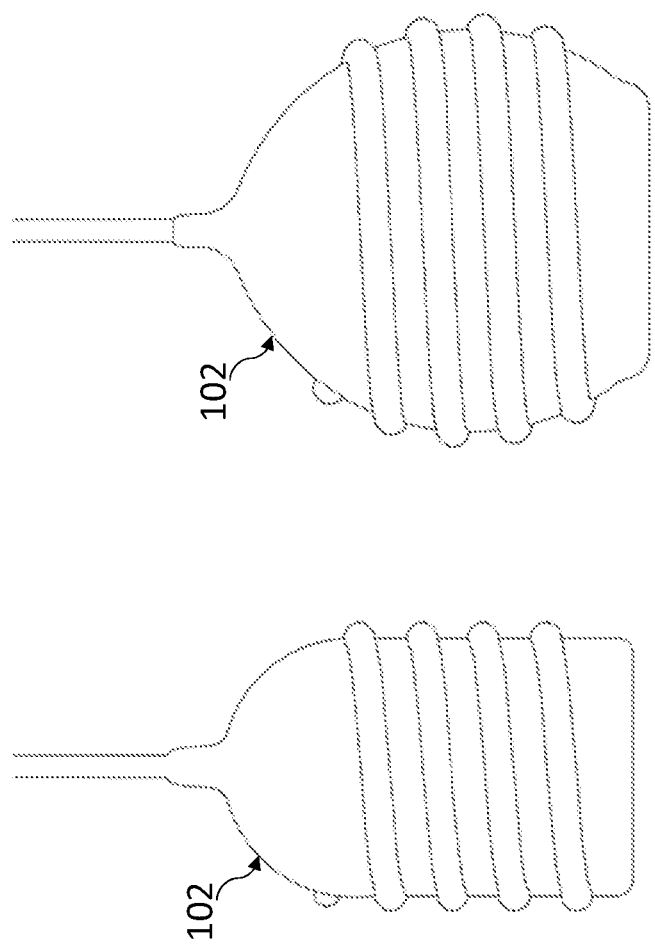
FIG. 19 is a schematic illustration of an inflation buoy with a corkscrew-shaped outer surface, according to an embodiment of the invention.
Figure 20:
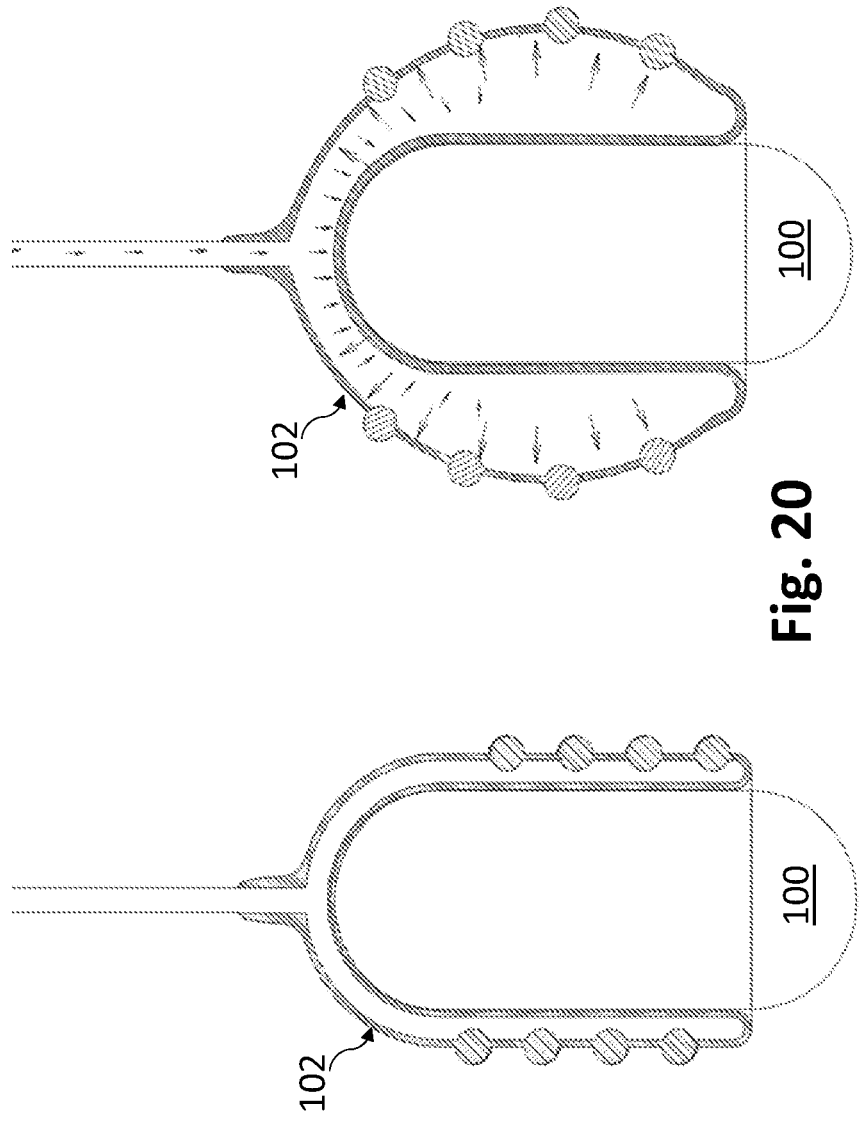
FIG. 20 is a schematic illustration an inflatable in-vivo capsule endoscope with a corkscrew-shaped inflation buoy in an uninflated state (left image) and an inflated state (right image), according to an embodiment of the invention.
Figure 21:
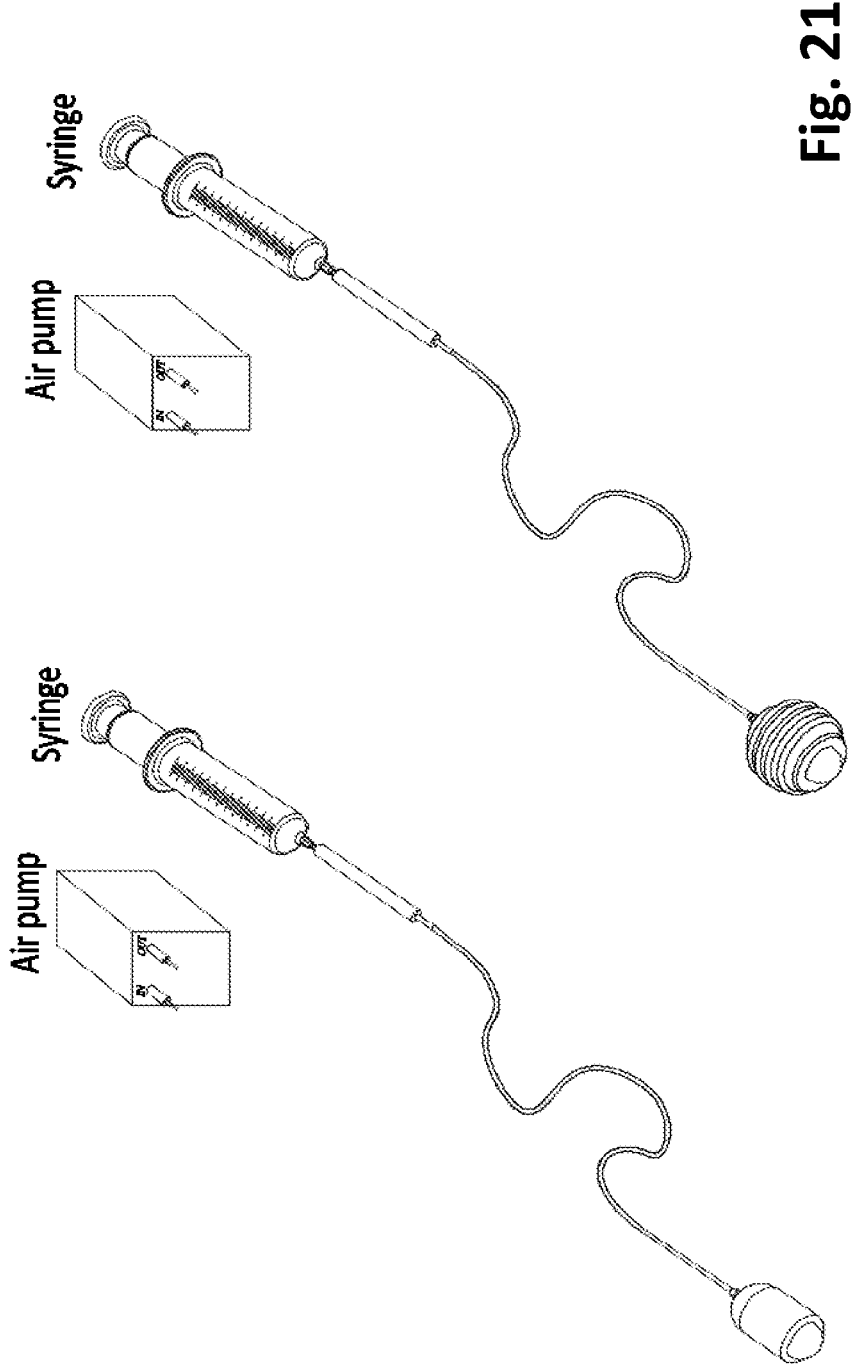
FIG. 21 is a schematic illustration of a tethered system for attaching a corkscrew-shaped inflation buoy to an ex-vivo inflation device via an elongated tether, according to an embodiment of the invention.

In some embodiments, the degree of inflation may be tuned or adjusted so that the capsule floats at various depths relative to the liquid surface (see e.g., FIGS. 16 and 18). Inflation device 112 may inject or expel gas to a desired volume or pressure to (automatically or manually) tune the floatation height level of the inflatable in-vivo capsule endoscope relative to the height level of the liquid. For example, to avoid distortions in the images cause by refraction at the liquid surface, buoy 102 may be inflated by a volume or pressure of gas so that capsule 100 floats to a liquid level that is sufficiently high while remaining completely submerged (see e.g., the middle height of the capsule in FIGS. 16 and 18).

Buoy 102 may be integral, fitted, or attached to an outer surface of a capsule-shaped body 104. Buoy 102 may have various sizes and shapes, such as, concave, cup-shaped, U-shaped cross-section, torus-shaped (when inflated) and cylindrical-shaped (when deflated), spherical, ellipsoidal, etc. Buoy 102 may also be positioned along various locations of capsule-shaped body 104, such as, surrounding the capsule's center of mass, encapsulating a minimal capsule surface area to securely attach (e.g., near an edge of the capsule, maximally spaced from the capsule's center of mass), encapsulating a maximum capsule surface area while avoiding occluding the sensing device (e.g., wrapping the entire capsule body, except the sensing device window), encapsulating any percentage of the capsule surface area, etc. Capsule-shaped body 104 may house the sensing device for capturing in-vivo images behind a transparent window or portion of the outer capsule surface 108. In one embodiment, buoy 102 may surround or encapsulate a portion of the outer capsule surface 106 such that it does not block or occlude the transparent portion of the outer capsule surface 108 (e.g., outside of the field of view of the sensing device). For a unidirectional or one-sided sensing device (e.g., with a camera system at only one longitudinal end of the capsule, e.g., as shown in FIG. 4), buoy 102 may have a concave shape or a U-shaped cross-section that surrounds the capsule's side walls and end 106 (e.g., as shown in FIG. 1), leaving the sensing device end 108 unobstructed. For a bidirectional or two-sided sensing device (e.g., with two camera systems at the two respective opposite longitudinal ends of the capsule) as shown in FIGS. 33-43, buoy 102 may have a torus, ring, or cylindrical shape to cradle or encapsulate the capsule's longitudinal center, but not block the sensing devices at either longitudinal end of the capsule. In another embodiment, buoy 102 may substantially transparent and may partially or fully overlap or cover the sensing device's field of view. A fully overlapping buoy 102 may be ellipsoidal or capsule shaped.

After imaging the stomach or other liquid-filled cavities in buoy's 102 inflated state, buoy 102 may be deflated to return the capsule to a partially or fully uninflated state, so that it can fit through smaller channels (e.g., either to be retracted backwards through the esophagus via a tether or to continue to progress forwards autonomously through the GI tract).

Reference is made to FIG. 4, which schematically illustrates an exploded view of inflatable in-vivo capsule endoscope 100 and components thereof, e.g., housed internal to capsule-shaped body 104, according to an embodiment of the invention. Capsule-shaped body 104 may have a longitudinal axis 111 along its longest length and a radial axis 121 along a diameter of its circular cross-section. Capsule-shaped body 104 may have two concave shells or hemispheres at opposite ends of its longitudinal axis 111. At one end of its longitudinal axis 111, capsule-shaped body 104 may have a shell 108 that is a transparent window for housing its sensing device 128. Sensing device 128 may comprise one or more image sensor(s), light source(s) (e.g., light emitting diodes (LEDs)), lens(es), for capturing in-vivo images, along with associated processing circuit board(s) for processing, storing, and/or sending image data. At the opposite end of its longitudinal axis 111, capsule-shaped body 104 may have a shell 106 that is either transparent (in a dual-camera endoscope) or opaque (in a single-camera endoscope). Capsule-shaped body 104 may also house one or more permanent magnet(s) 124 having a permanent magnetic dipole (e.g., North-South). Permanent magnets 124 allow capsule endoscope 100 to be magnetically guided when exposed to a magnetic field generated by one or more external magnets 126 (e.g., as shown in FIG. 5). Capsule-shaped body 104 may also house a wireless communication system 122 comprising a wireless (e.g., radio frequency (RF)) processing board and an antenna for wirelessly transmitting and receiving information to/from a remote device or controller. Wireless communication system 122 may transmit in-vivo information, such as, in-vivo image data captured by sensing device 128, buoy 102 values or parameters such as pressure or gas volume, magnetic field information for interacting with and being controlled by external magnet control system 126, and/or other sensory feedback, e.g., in-vivo conditions such as temperature, pressure, pH, etc. Wireless communication system 122 may receive commands or control information from an external device, such as, inflation or deflation activation commands for an autonomous in-vivo inflation device 112 and/or image capture commands or parameters. Capsule-shaped body 104 may also house one or more batteries or a power supply 132 to power the endoscope 100 components.

Reference is made to FIG. 5, which schematically illustrates an external magnetic control system 126, according to an embodiment of the invention. External magnetic control system 126 may generate a magnetic field to guide capsule endoscope 100 via one or more permanent magnet(s) 124 contained in capsule endoscope 100. External magnetic control system 126 includes fixtures adapted for horizontal and vertical positioning of one or more external permanent magnet(s) 134 by the use of vertically and horizontally adjustable mechanisms and an adjustable base. External magnetic control system 126 has freedom of movement along two axes to move capsule endoscope 100 in three dimensions. Details of the mechanics and operation of external magnetic control system 126 may be described, for example, in U.S. Patent Application Publication No. 2015/0380140, the entirety of which is hereby incorporated by reference.

When capsule endoscope 100 is inflated and floating in liquid, its buoyancy makes the capsule significantly easier to move magnetically. Accordingly, external magnetic control system 126 can be significantly smaller, and its magnetic field can have significantly smaller magnitude, than is used in conventional external capsule-guiding magnet systems. For example, external permanent magnet(s) 134 may have a magnetic moment M that is approximately 75 A/cm$^2$ (significantly smaller than the 2500 A/cm$^2$, which would conventionally be used for comparable motion if the capsule was uninflated) and a diameter of 5 cm (significantly smaller than the 16 cm, which would conventionally be used for comparable motion if the capsule was uninflated). In some embodiments, external magnetic control system 126 may be small enough to be a handheld or portable device.

Inflatable in-vivo capsule endoscope 100 may be deployed in a tethered system (e.g., as shown in FIGS. 2-3, 6-21, 23-26, and 28) or an autonomous (untethered) system (e.g., as shown in FIGS. 29-32). It may be appreciated that details of capsule endoscope 100 described in the context of a tethered system also apply to the context of an autonomous (untethered) system (and vice versa), unless specifically part of, or reliant upon, the tether or autonomous inflating components or functionalities.

Figure 6:
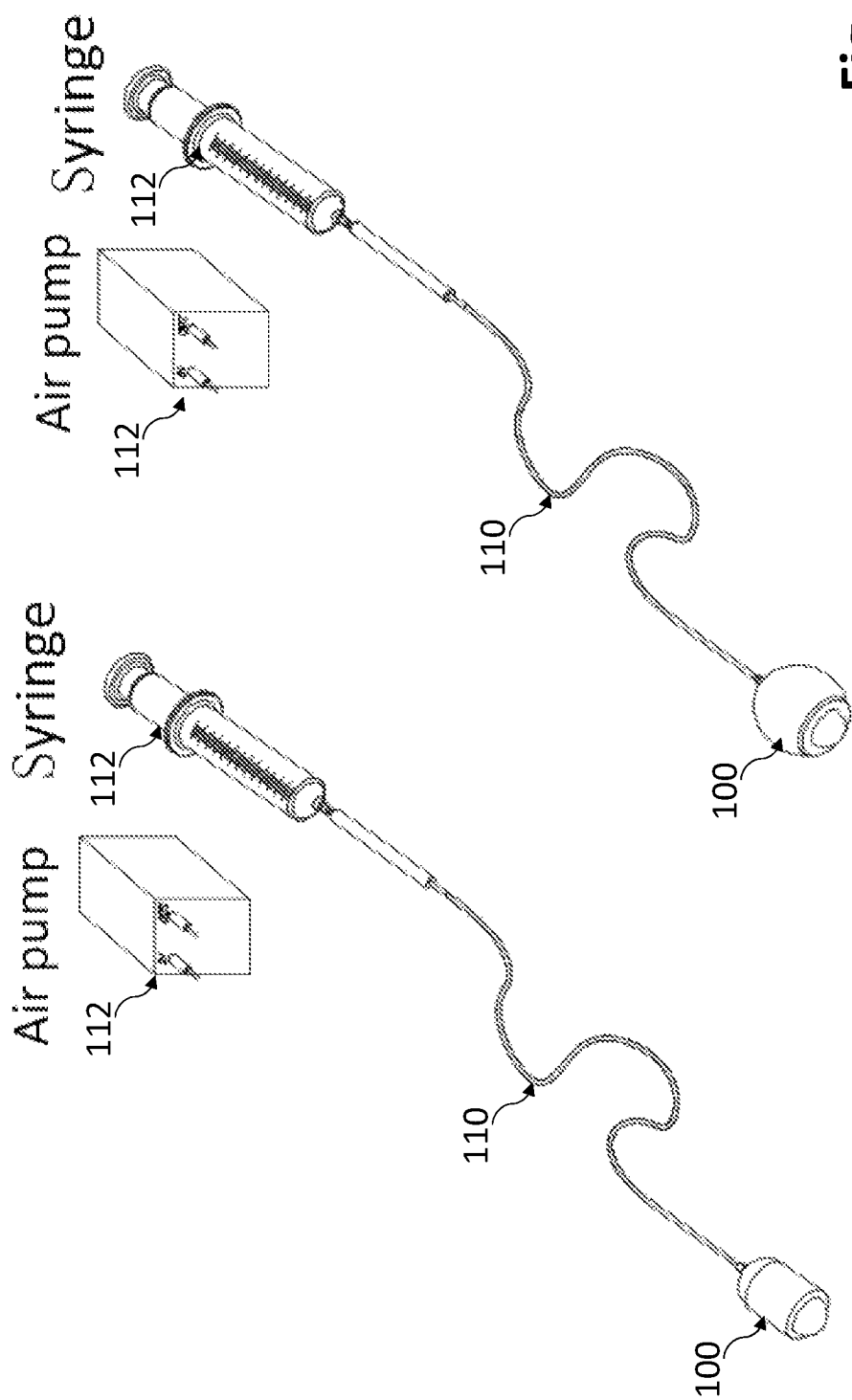
FIG. 6 is a schematic illustration of a tethered system for attaching in-vivo buoy to an ex-vivo inflation device via an elongated tether, according to an embodiment of the invention.

Reference is made to FIG. 6, which schematically illustrates a tethered system for attaching in-vivo buoy 102 to an ex-vivo inflation device 112 via an elongated tether 110, according to an embodiment of the invention. Tether 110 may traverse a portion of the GI tract of the organism and may connect ex-vivo inflation device 112 (positioned outside of an organism) to the in-vivo inflatable buoy 102 (positioned inside of the organism) when inflating buoy 102. Ex-vivo inflation device 112 (on the end of tether 110 opposite capsule 100) may comprise a syringe, air pump, air compressor, chemical gas reactor, and/or liquid injection pump, tank, or rubber bulb. Inflation device 112 may adjust the air pressure or volume in buoy 102, adjust the floatation height or level relative to the water level, and/or adjust the pressure or size of a corkscrew-shaped buoy to fit variable sized channels, such as the esophagus or small bowel.

Figure 7:
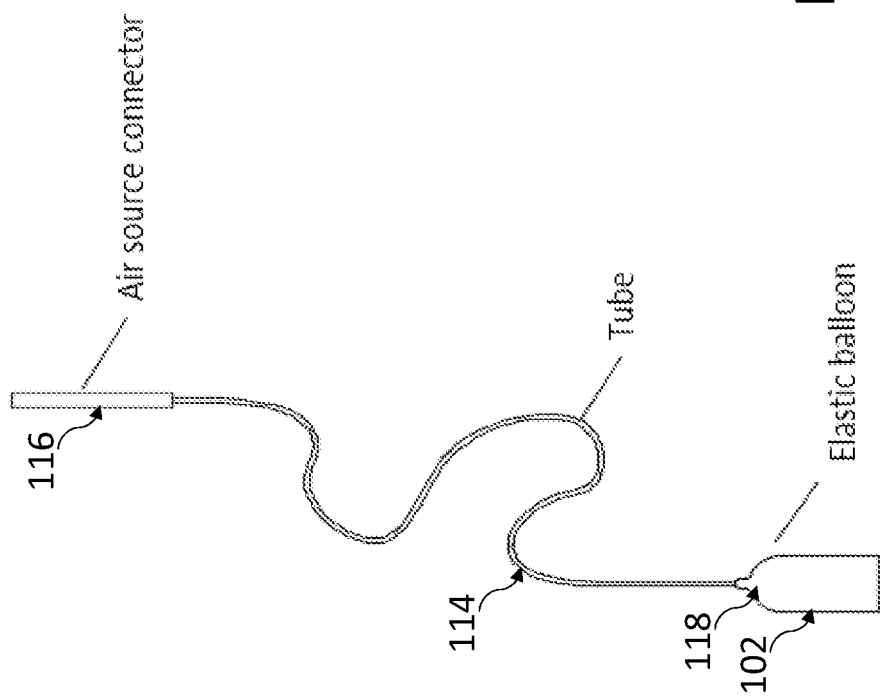
FIG. 7 is a schematic illustration of a tether for attaching in-vivo buoy to ex-vivo inflation device, according to an embodiment of the invention.
Figure 8:
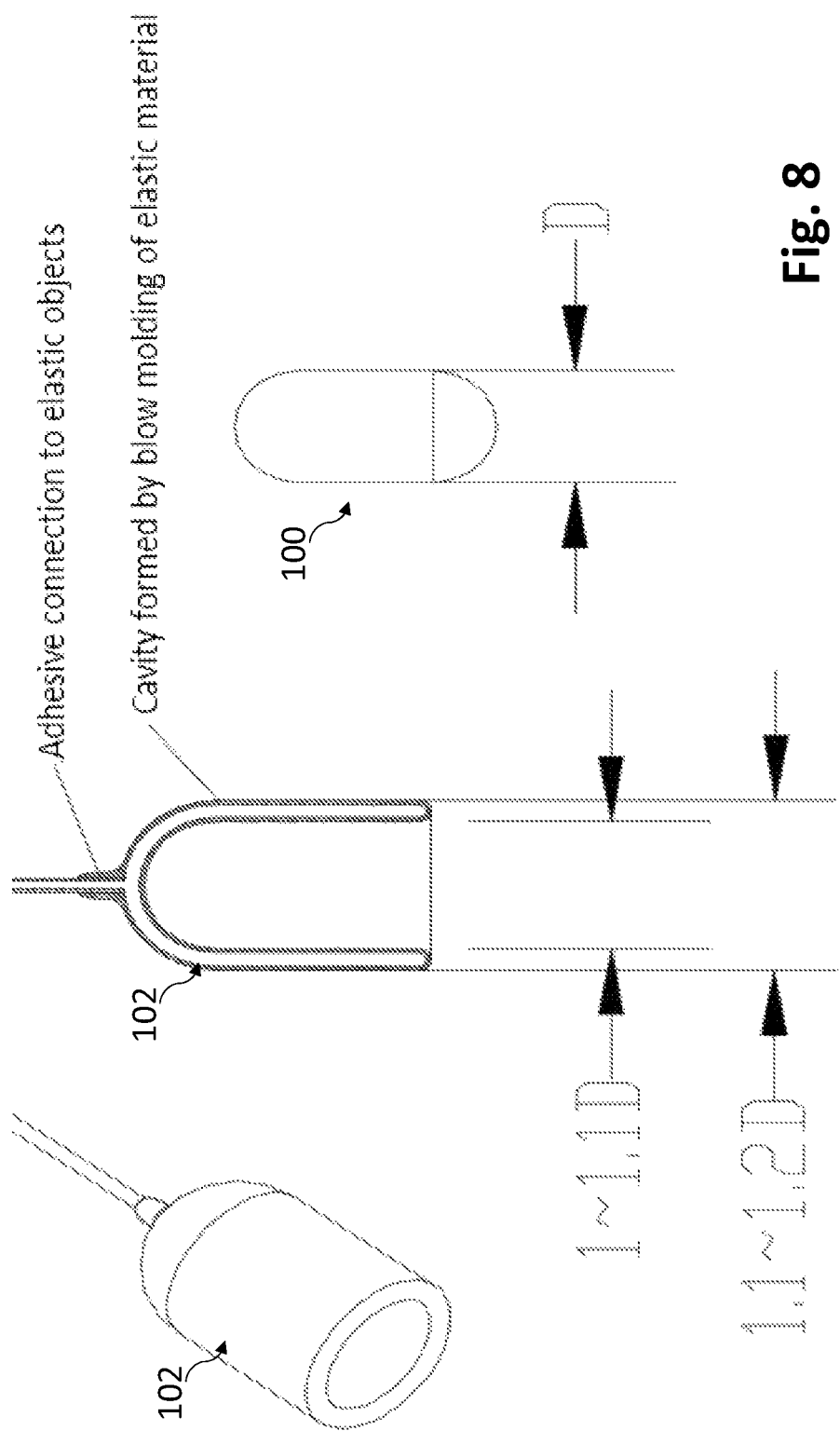
FIGS. 8-11 are schematic illustrations of a "balloon expansion" type buoy that attaches to the capsule-shaped body by adhesion, according to an embodiment of the invention.
Figure 9:
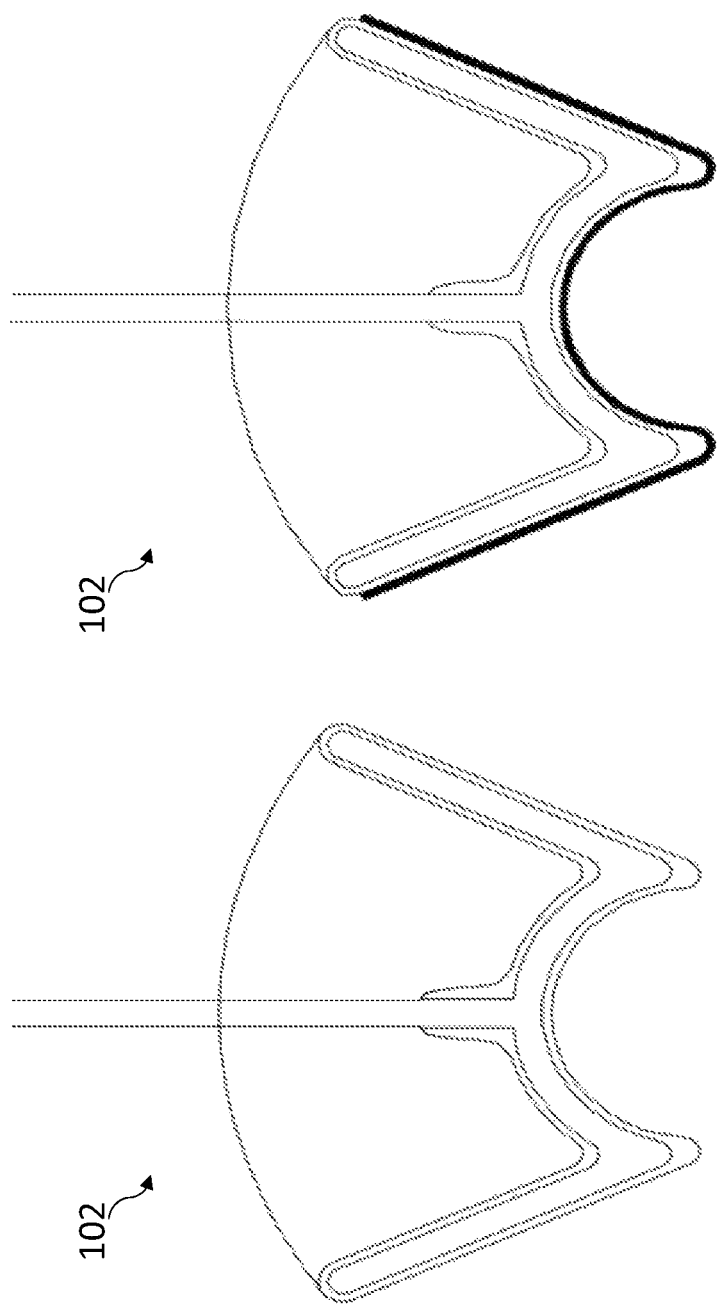
Figure 10:
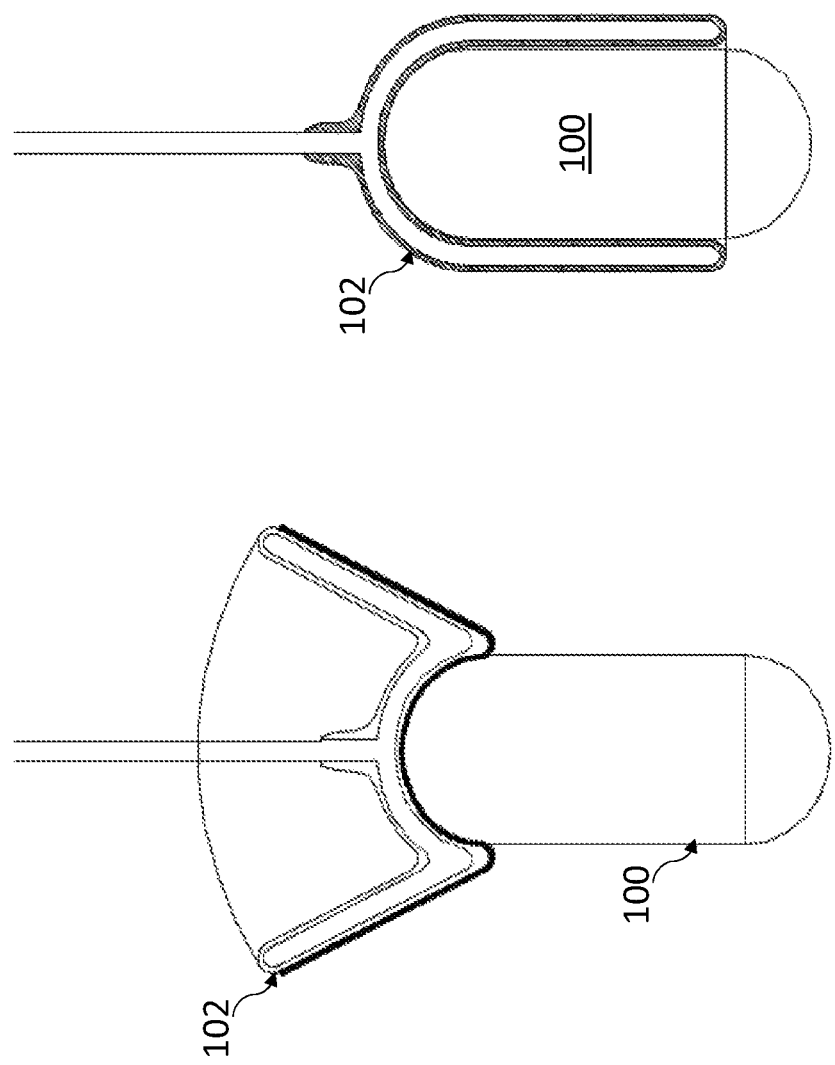
Figure 11:
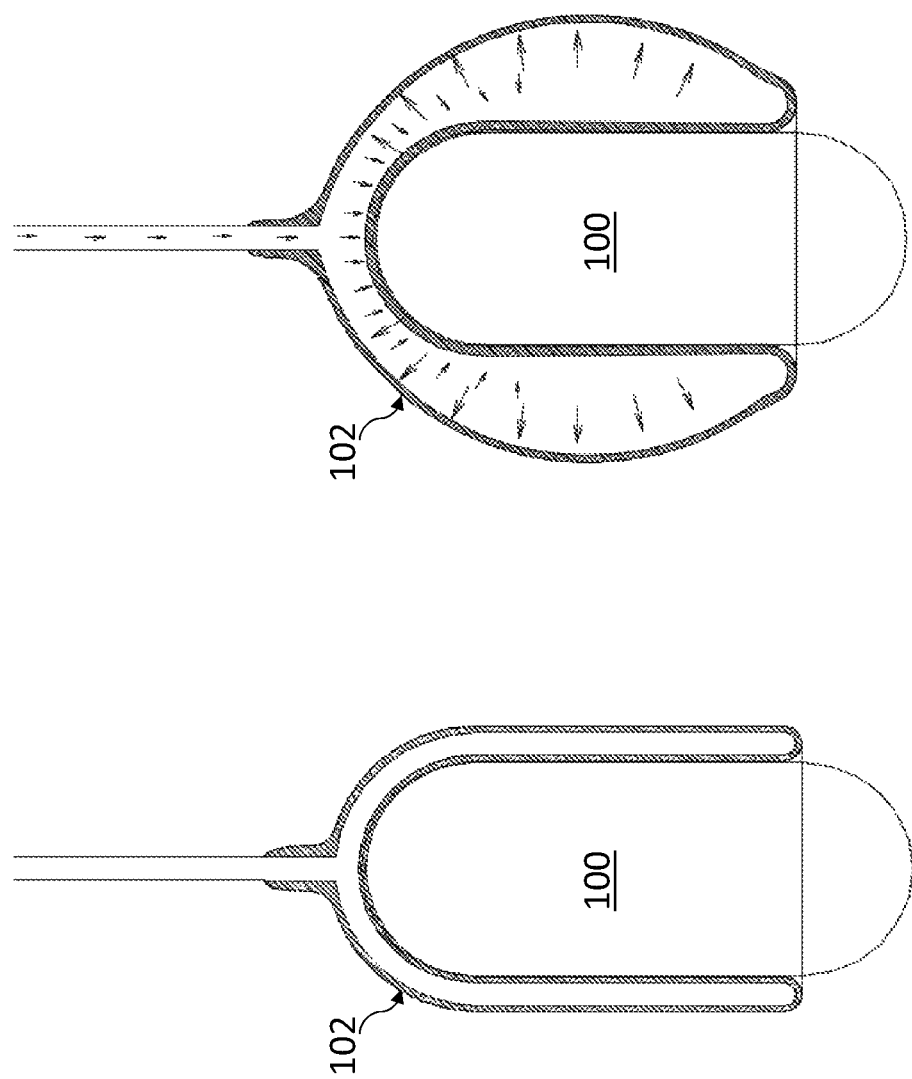
Figure 12:
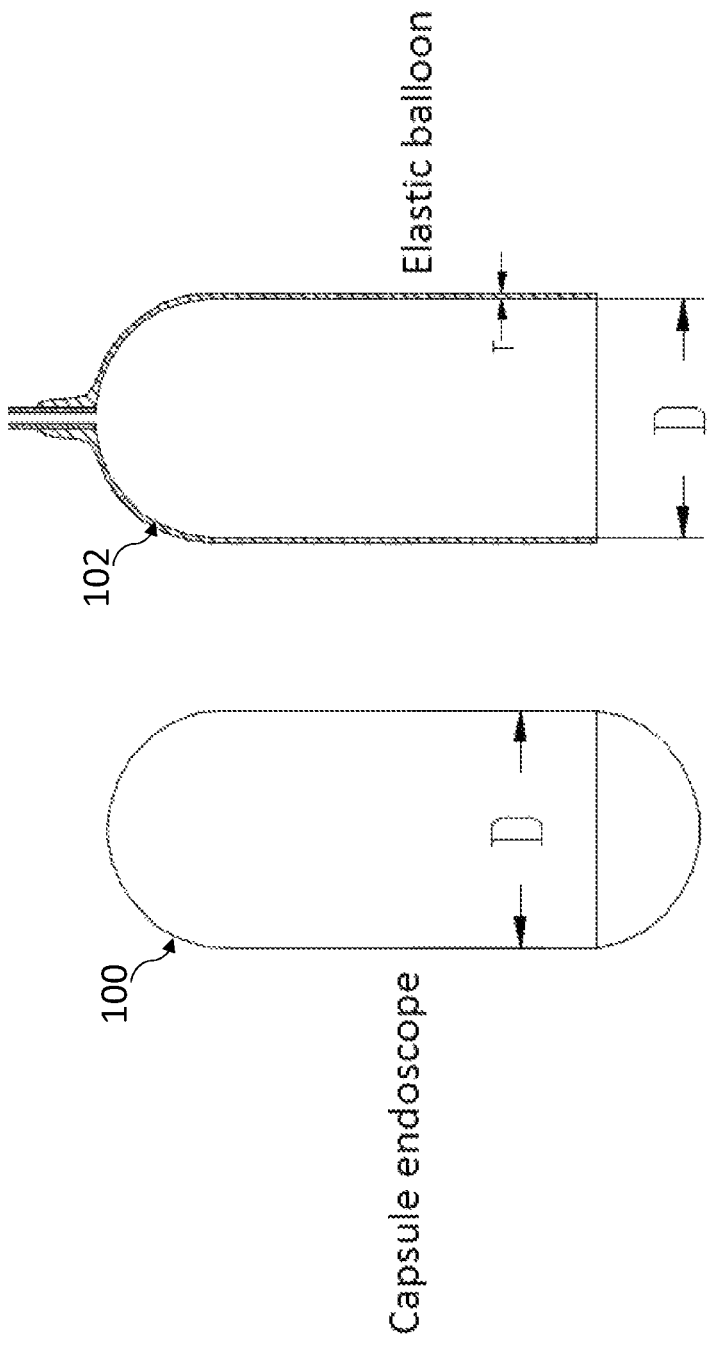
FIGS. 12-14 are schematic illustrations of a "cup expansion" type buoy that attaches to the capsule-shaped body by elastic tension, according to an embodiment of the invention.
Figure 13:
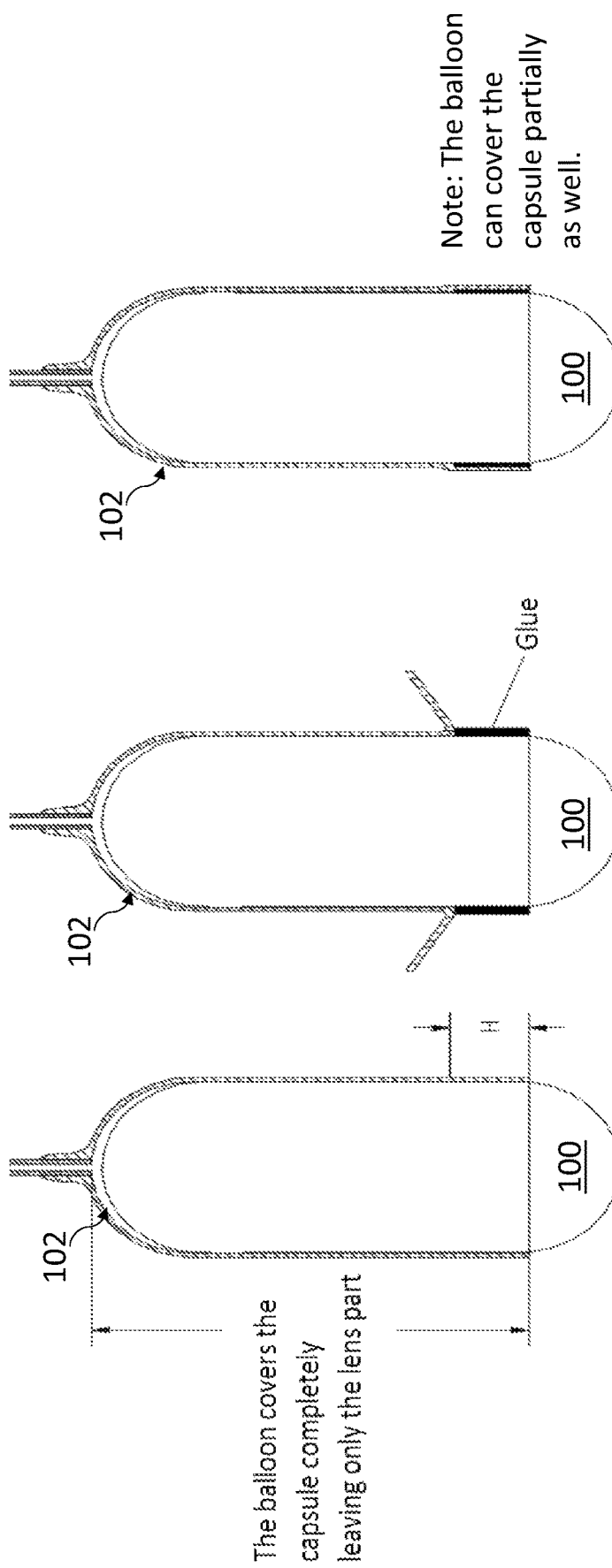
Figure 14:
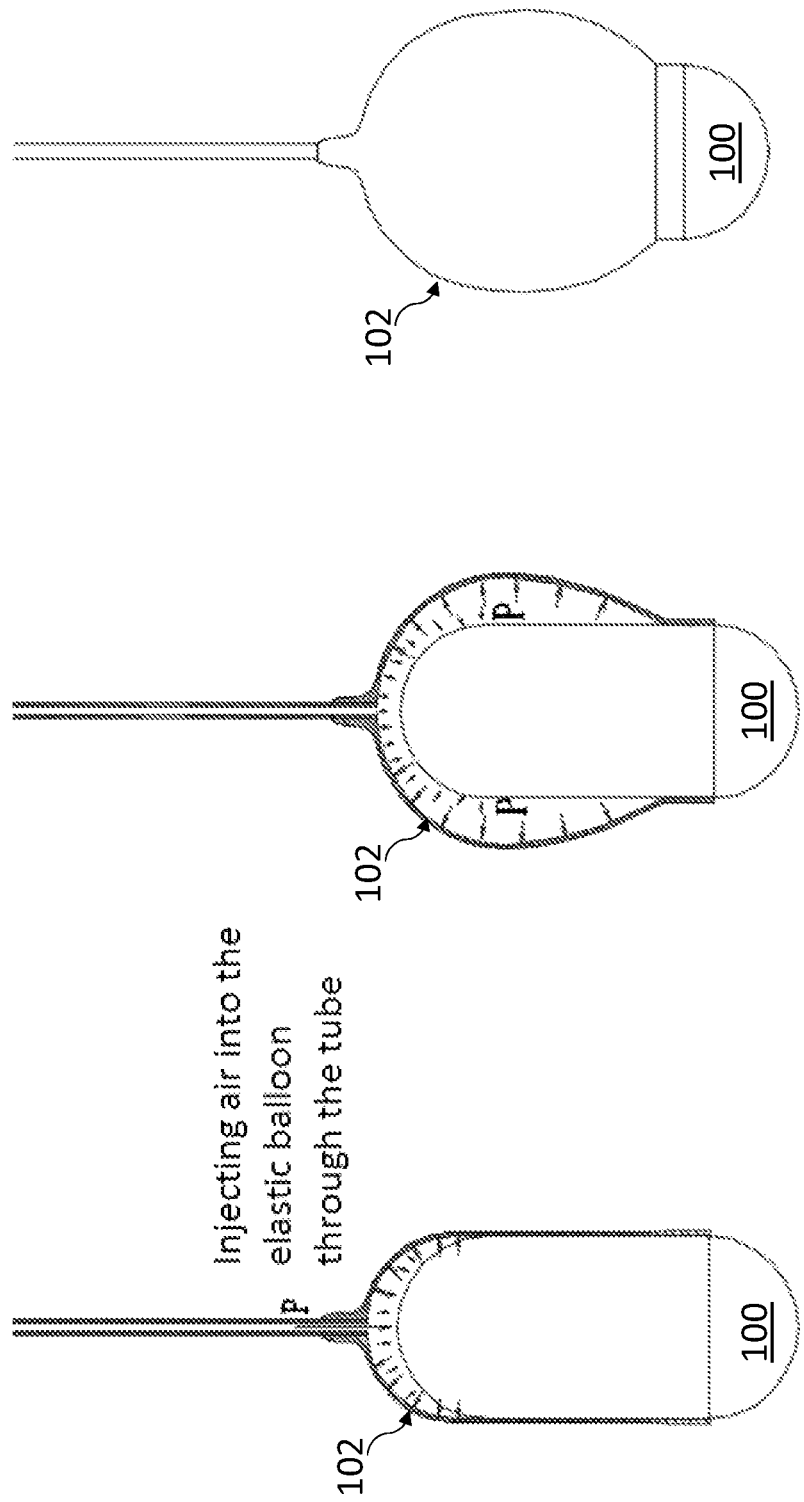

Reference is made to FIG. 7, which schematically illustrates a tether 110 for attaching in-vivo buoy 102 to ex-vivo inflation device 112, according to an embodiment of the invention. Tether 110 may have an extension tube 114 comprising a first end 116 that connects to inflation device 112 and a second end 118 that connects to buoy 102. Extension tube 114 may be an elongated air-tight channel to transport gas from inflation device 112 to buoy 102 (for inflation) and/or extract or suction gas from buoy 102 to a deflation device (the same or different as inflation device 112) (for deflation). Tether 110 may have a fixed length or retractable (variable length) extension tube 114. When fully extended, tether 110 may span a distance at least long enough to stretch from outside of an organism's mouth to inside of a target channel or cavity inside the organism, such as, the stomach. The second end 118 connecting tether 110 and buoy 102 may be permanently attached (e.g., glued or affixed such that separation may break or damage the system or its components) or may be releasable (e.g., detachable by air pressure above a threshold volume or force, or by magnetic force, without breaking or damaging the system or its components). An example of a magnetically releasable second end 118 connecting tether 110 and buoy 102 is described in reference to FIG. 28.

Reference is made to FIGS. 8-14, which schematically illustrate various types of inflatable buoys 102, according to an embodiment of the invention. Inflatable buoy 102 may have an air-tight bladder including one or more membranes that seal to hold gas. Inflatable buoy 102 may have an inflation/deflation port through which gas flows. Inflation/deflation port may be part of (or connected to) elongated tube 114 in a tether system or a hole 120 in an autonomous (untethered) system. Inflatable buoy 102 may connect to capsule-shaped body 104 by a sealant (e.g., adhesive) or elastic tension. In one embodiment of a sealant connection shown in FIGS. 8-11, buoy 102 may inflate by "balloon expansion," wherein two layers of membrane of buoy 102 form an enclosed bladder. The two layers of membrane are relatively thinly spaced and comprise tight elastic material, forming an elastic seal with capsule-shaped body 104. The balloon expansion buoy 102 may inflate relatively evenly throughout the bladder. In one embodiment of an elastic connection shown in FIGS. 12-14, buoy 102 may inflate by "cup expansion," wherein a bladder is formed by sealing a one layer membrane of buoy 102 to the outer surface of capsule-shaped body 104 e.g., via an adhesive. The cup expansion bladder may inflate more towards the back end 106 of the capsule, thus forming a cup shaped bladder, leaving the front end sealed. Although specific buoy dimensions are shown in the figures, those dimensions are only shown as examples and other dimensions may be used. The dimensions of the bladders may be made to modified to fit a capsule device of any size or shape.

Figure 15:
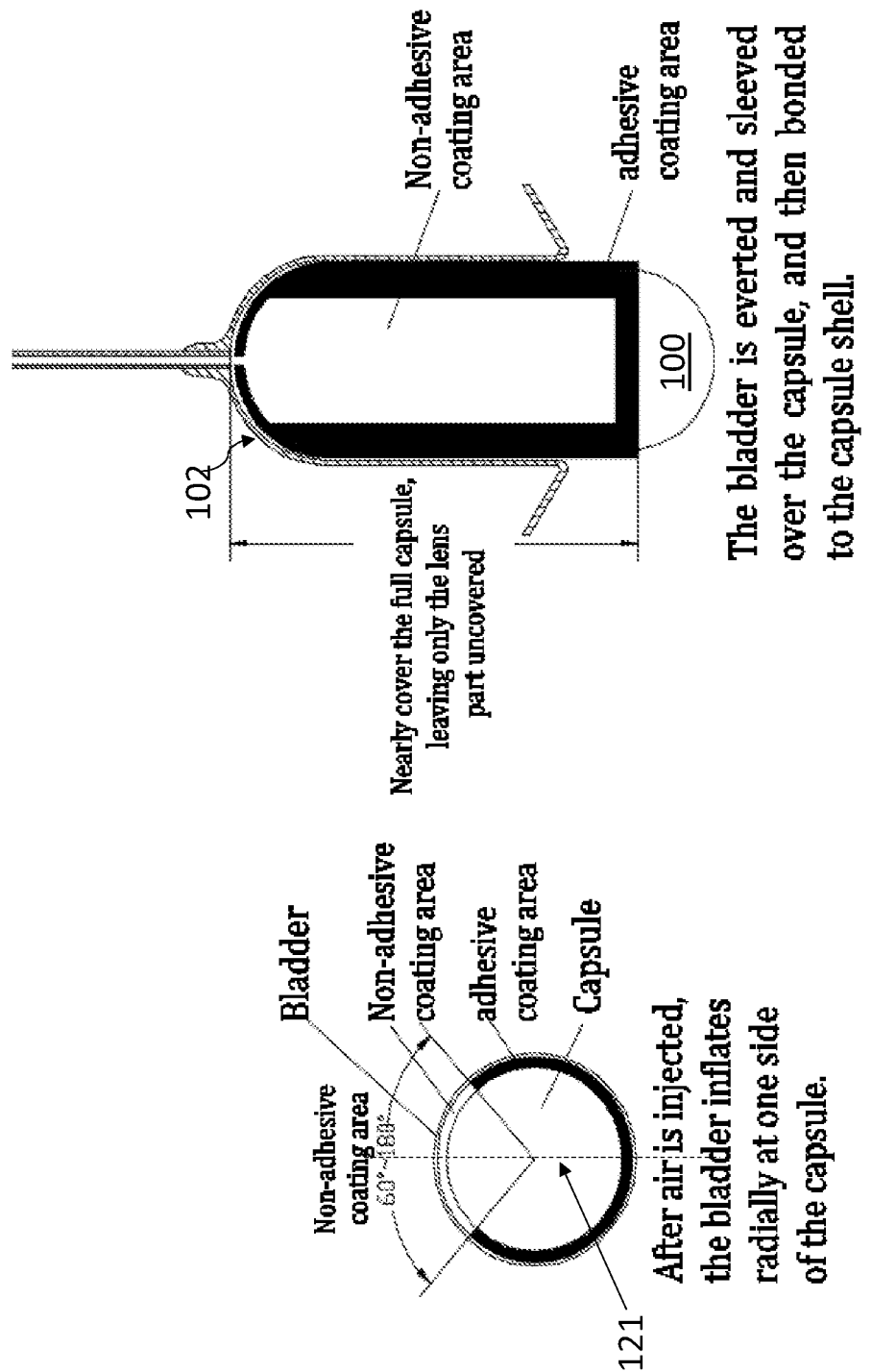
FIGS. 15-16 are schematic illustrations of a radially asymmetric inflation buoy, according to an embodiment of the invention.

Reference is made to FIGS. 15-18, which schematically illustrate an inflation buoy 102 positioned asymmetrically (or that inflates asymmetrically) relative to a radial axis 121, according to an embodiment of the invention. An asymmetric inflation buoy 102 may have an end that rises to a relatively higher liquid level compared to the rest of the capsule to orient the capsule-shaped body 104 (e.g., top-up), and thus the image field of view. Because the images are collected in a righted field of view, image processing need not re-orient the images (or may reduce re-orientation processing) to speed up image processing. In FIGS. 15-16, inflation buoy 102 is asymmetric about radial axis 121, but symmetric or centered about its longitudinally axis 111. Thus, when inflated, capsule 100 has a predefined highest radial position, but floats level about longitudinally axis 111. In FIGS. 17-18, inflation buoy 102 is asymmetric about both its radial axis 121 and its longitudinally axis 111. Thus, when inflated, capsule 100 has a predefined highest radial and longitudinal positions.

Figure 30:
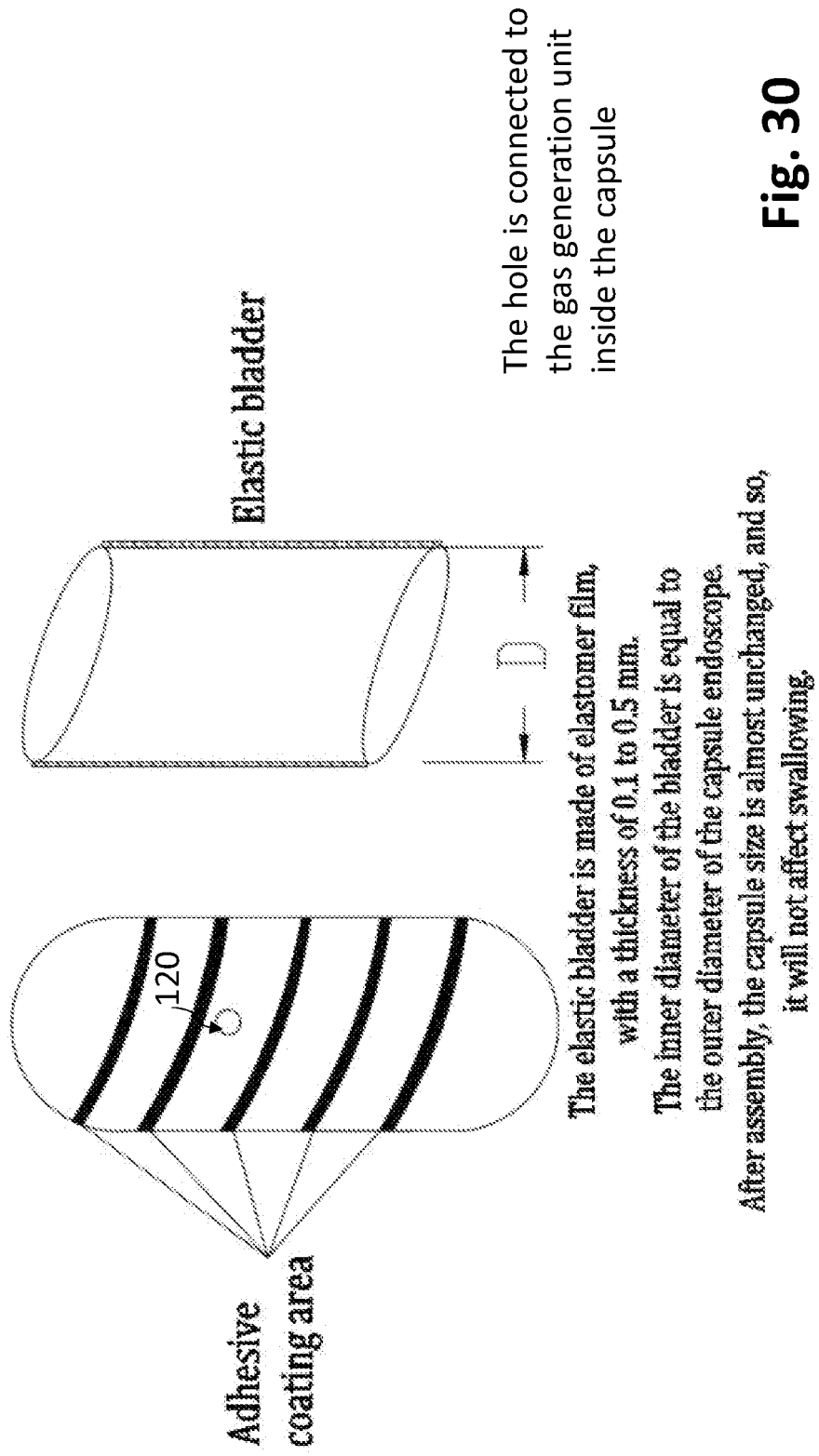
FIG. 30 is a schematic illustration an autonomous capsule endoscope comprising an adhesive coating for adhering a corkscrew-shaped elastic bladder, according to an embodiment of the invention.
Figure 31:
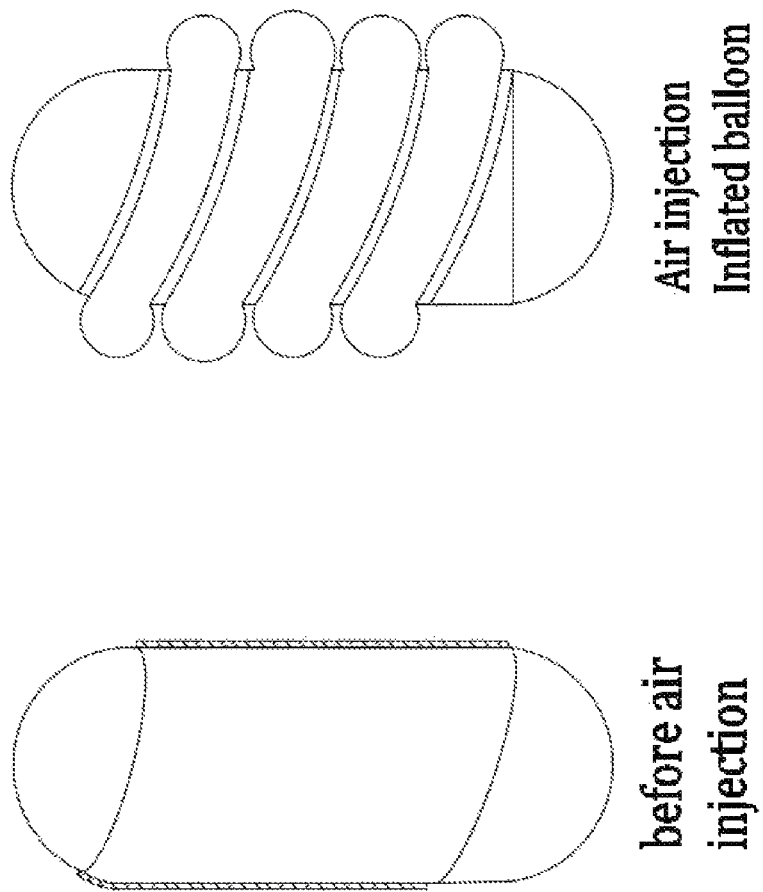
FIG. 31 is a schematic illustration of an autonomous capsule endoscope comprising an uninflated elastic corkscrew buoy (left image) and an inflated elastic corkscrew buoy (right image), according to an embodiment of the invention.

Reference is made to FIGS. 19-21, 23-27 and 30-31, which schematically illustrate an inflation buoy 102 with a corkscrew-shaped outer surface, according to an embodiment of the invention. Corkscrew-shaped buoy 102 has a spiral threading protruding along the outer-surface of the buoy. The spiral threading may rotate clockwise or counterclockwise from a first longitudinal end to an opposite longitudinal end of the capsule (or a portion thereof). Corkscrew-shaped buoy 102 may be implemented in a tethered system (e.g., as shown in FIGS. 19-21 and 23-27) or an autonomous (untethered) system (e.g., as shown in FIGS. 30-31). External magnet control system 126 may exert a magnetic force on the capsule's internal permanent magnet(s) 124 to guide capsule endoscope 100 through a channel, such that when buoy 102 is inflated, the spiral threading propels inflatable in-vivo capsule endoscope 100 forward or backwards by rotating in a spiral motion.

Figure 27:
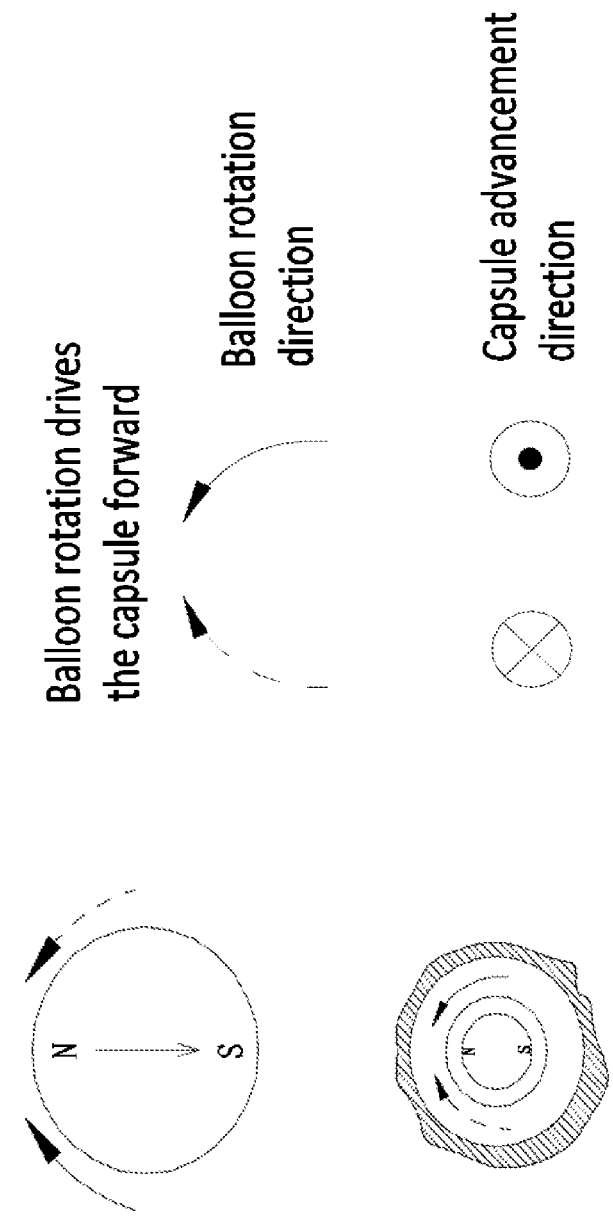
FIG. 27 is a schematic illustration of a relationship between the direction of rotation of a corkscrew-shaped capsule endoscope and the direction of translational propulsion of the corkscrew-shaped capsule endoscope, according to an embodiment of the invention.

Reference is made to FIG. 27, which schematically illustrates an example relationship between the direction of rotation of the spiraling corkscrew-shaped capsule endoscope 100 and the direction of translational propulsion of capsule endoscope 100, according to an embodiment of the invention. According to the example configuration shown in FIG. 27, the upper left drawing illustrates the external control magnet and the bottom left drawing illustrates the magnet inside of the capsule. The rotation of the fixed magnet inside the capsule may be opposite to the direction of the external magnet. When using a clockwise threading, a clockwise rotation of the capsule (counter-clockwise rotation of the external magnet) will propel capsule endoscope 100 forward (in a direction into the figure), and a counter-clockwise rotation of the capsule (clockwise rotation of the external magnet) will cause the capsule endoscope 100 to move backwards (in a direction out of the figure). Opposite directions of motion may be achieved using a counterclockwise threading. Other directional relationships may also be used. For example, the direction of threading may be inverted such that the corkscrew-shaped surface may propel capsule endoscope 100 forwards when rotating in a clockwise rotational direction and backwards when rotating in an opposite counterclockwise rotational direction.

Figure 22:
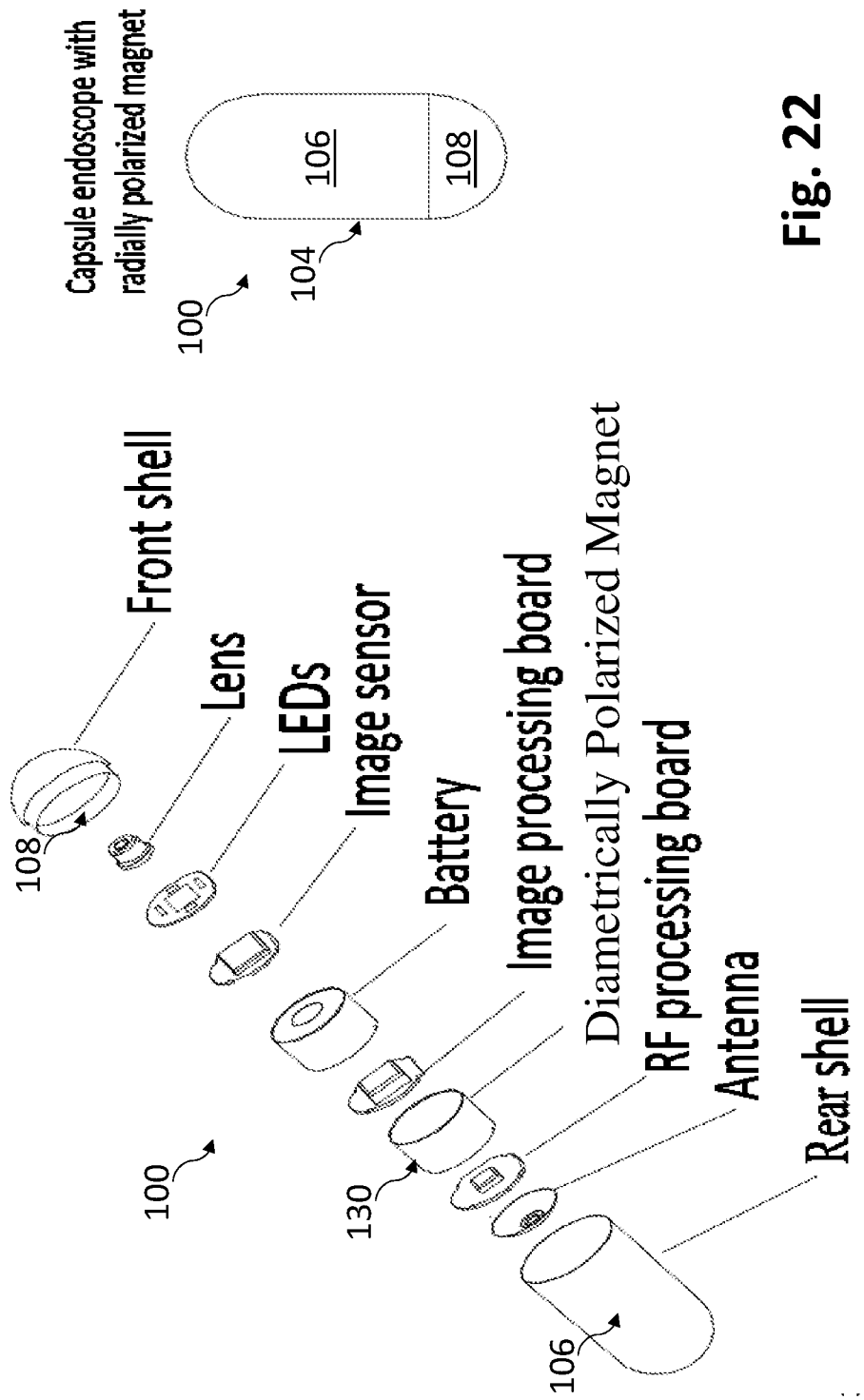
FIG. 22 is a schematic illustration of an exploded view of a corkscrew-shaped inflatable in-vivo capsule endoscope and components thereof including a diametrically polarized magnet, according to an embodiment of the invention.

Permanent magnet(s) 124 diametrically centered about radial axis 121 (e.g., as shown in FIG. 4) cause external magnets 126 to translate capsule endoscope 100 along the direction of longitudinal axis 111. Additionally or alternatively, as shown in FIG. 22, corkscrew-shaped capsule endoscope 100 may have a diametrically polarized magnet 130 (polarized in a diametric direction) having a position and/or dipole that is diametrically asymmetric with respect to radial axis 121 (along a circular cross-section of the capsule-shaped body) so that external magnets 126 rotate capsule endoscope 100 about its longitudinal axis 111, causing a spiraling or spinning force that further drives the capsule in a corkscrew-shaped motion.

Because the size of channels is variable throughout the GI tract, a constant size threading may not fit certain channels. For example, if the capsule diameter is too small compared to the channel diameter, there may not be sufficient tension to grip the capsule (see e.g., top image of FIG. 26), whereas if the capsule diameter is too large compared to the channel diameter, the capsule may get stuck in the channel. Accordingly, an optimal propulsive force depends on an optimal fit between the capsule endoscope 100 and the surrounding channel. To that end, buoy 102 may be inflated to an optimal diameter, tension, and/or pressure, relative to the channel, so that the channel may exert a maximal propulsive force on the capsule (see e.g., bottom image of FIG. 26). In one embodiment, inflation device 112 may inflate inflation buoy 102 to a diameter that substantially matches (or is slightly, e.g., 5-20%, larger than) a channel diameter and/or to achieve a target pressure between capsule endoscope 100 and the channel to propel the endoscope regardless of channel diameter. The target or optimal diameter, tension, pressure, may be detected automatically (e.g., via a pressure gauge connected to the inflation device 112) or manually.

Figure 23:
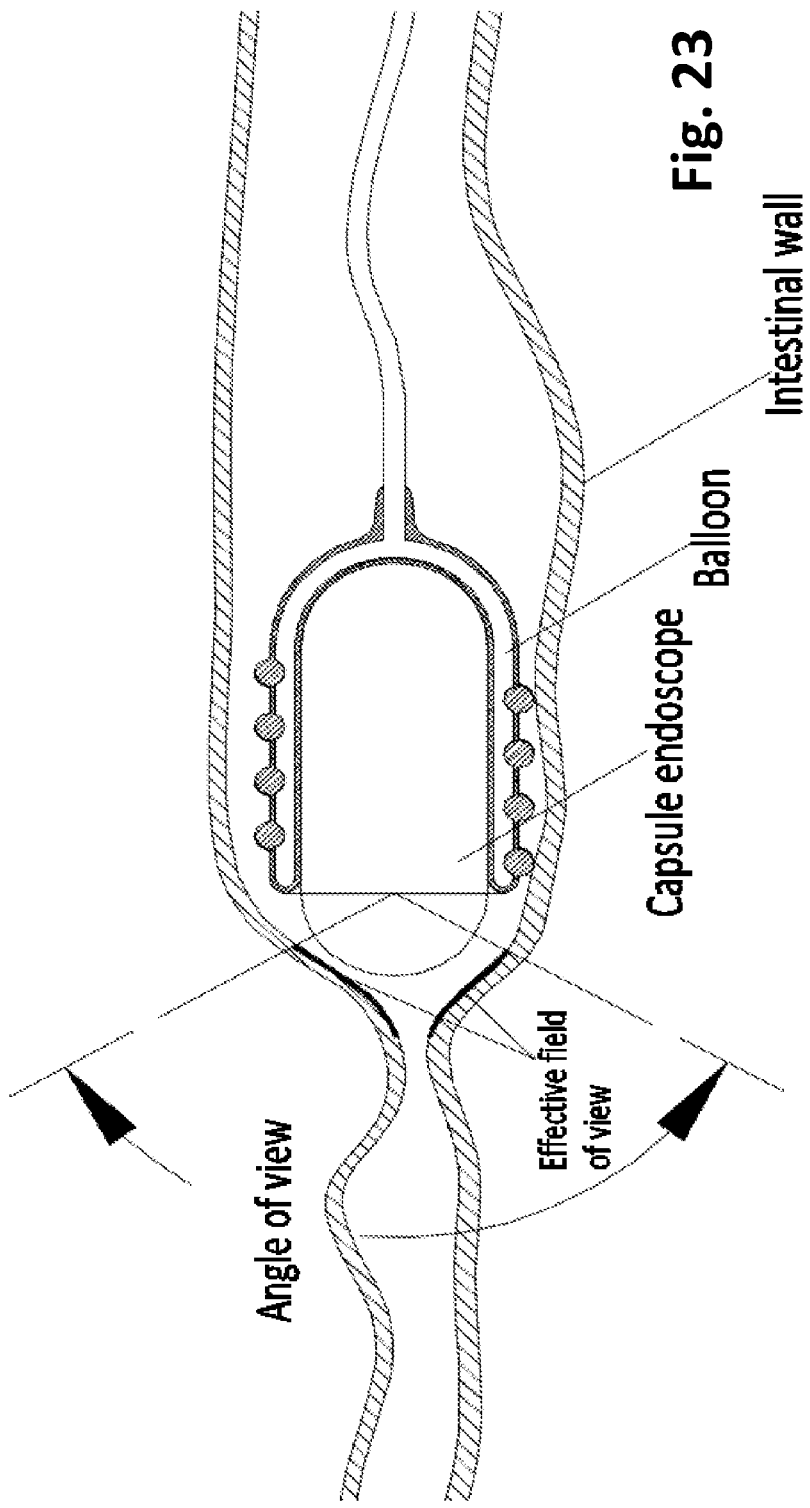
FIG. 23 is a schematic illustration of an uninflated corkscrew-shaped capsule endoscope in a narrow channel that obstructs the capsule's field of view, according to an embodiment of the invention.
Figure 24:
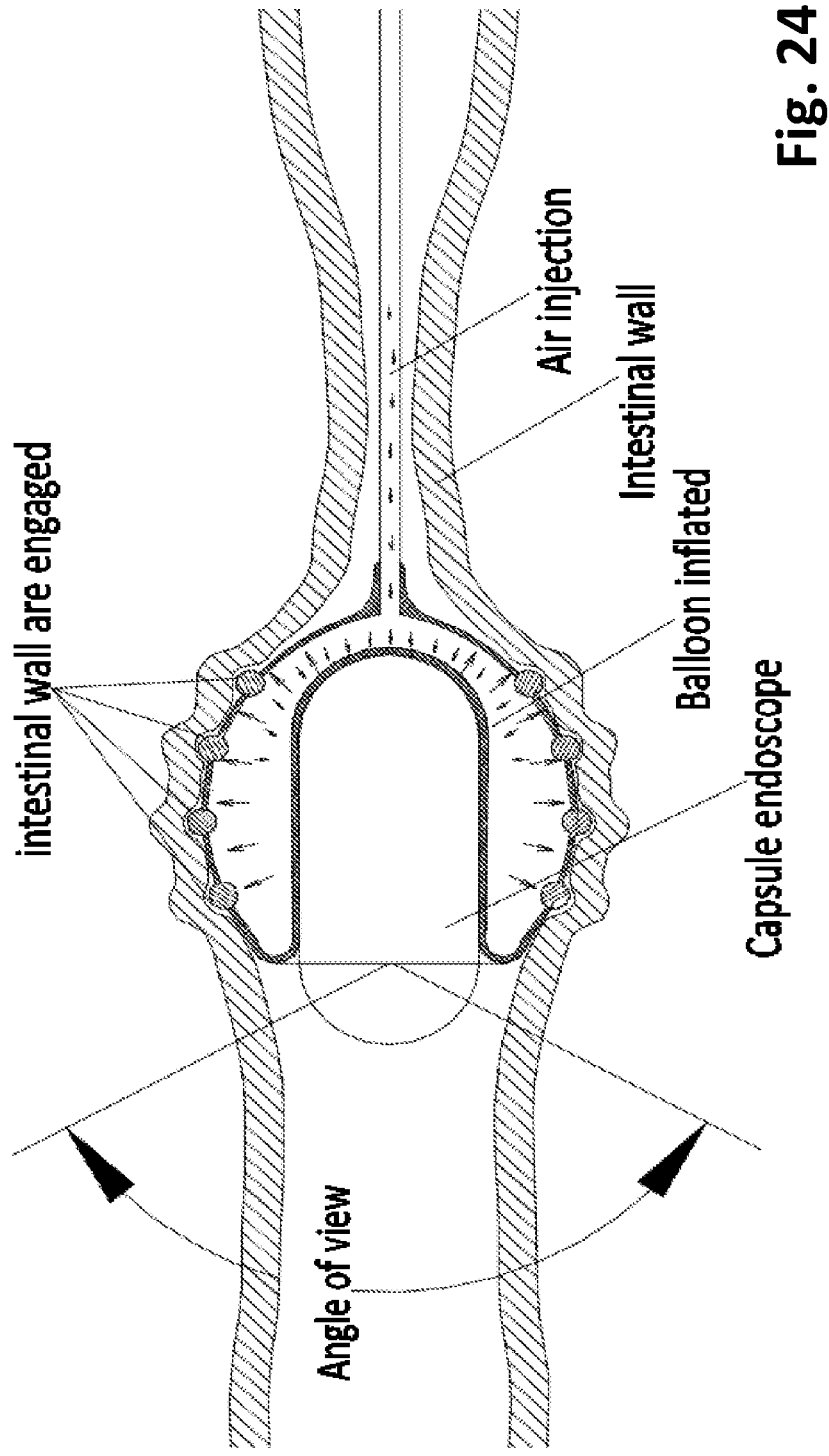
FIG. 24 is a schematic illustration an inflated corkscrew-shaped capsule endoscope that widens the channel to increase the capsule's field of view, according to an embodiment of the invention.
Figure 25:
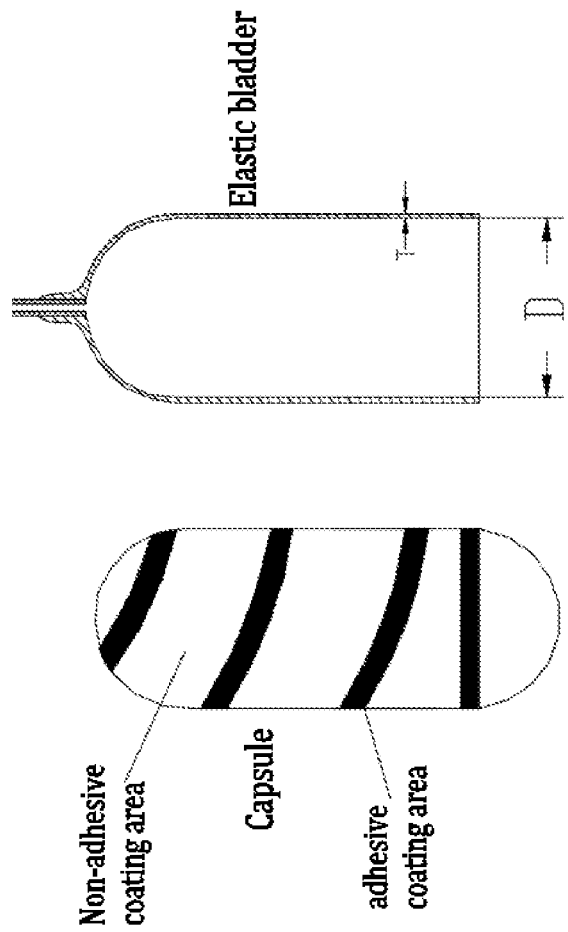
FIG. 25 is a schematic illustration of an uninflated corkscrew-shaped buoy with an elastic bladder, according to an embodiment of the invention.
Figure 26:
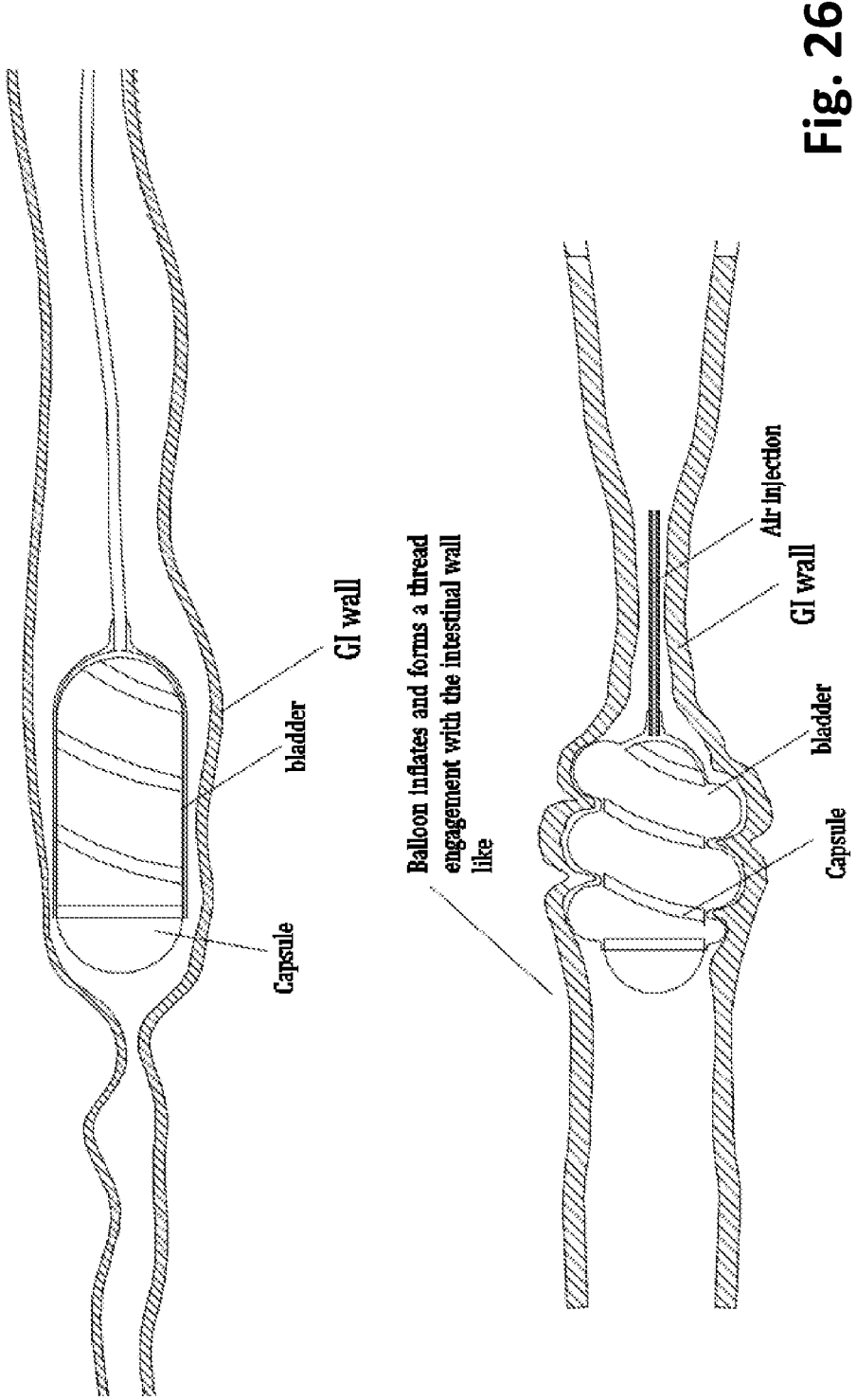
FIG. 26 is a schematic illustration a capsule endoscope travelling through a narrow channel with an uninflated elastic corkscrew buoy (top image) and an inflated elastic corkscrew buoy (bottom image), according to an embodiment of the invention.

Additionally or alternatively, inflating buoy 102 in narrow channels (e.g., having the same or smaller diameter than the capsule) may widen the channel to increase the effective field of view of the sensing device. Reference is made to FIGS. 23-24, which schematically illustrate an inflatable in-vivo capsule endoscope 100 in an uninflated state (FIG. 23) and an inflated state (FIG. 24), according to an embodiment of the invention. In FIG. 23, when the capsule endoscope 100 is in an uninflated state, narrow channel walls may obstruct the effective field of view (e.g., the visible space) of the organism to be significantly less than the sensing device's 128 angle of view. In FIG. 24, when the capsule endoscope 100 is in an inflated state, the channel walls are widened to significantly increase the sensing device's 128 effective field of view.

Figure 28:
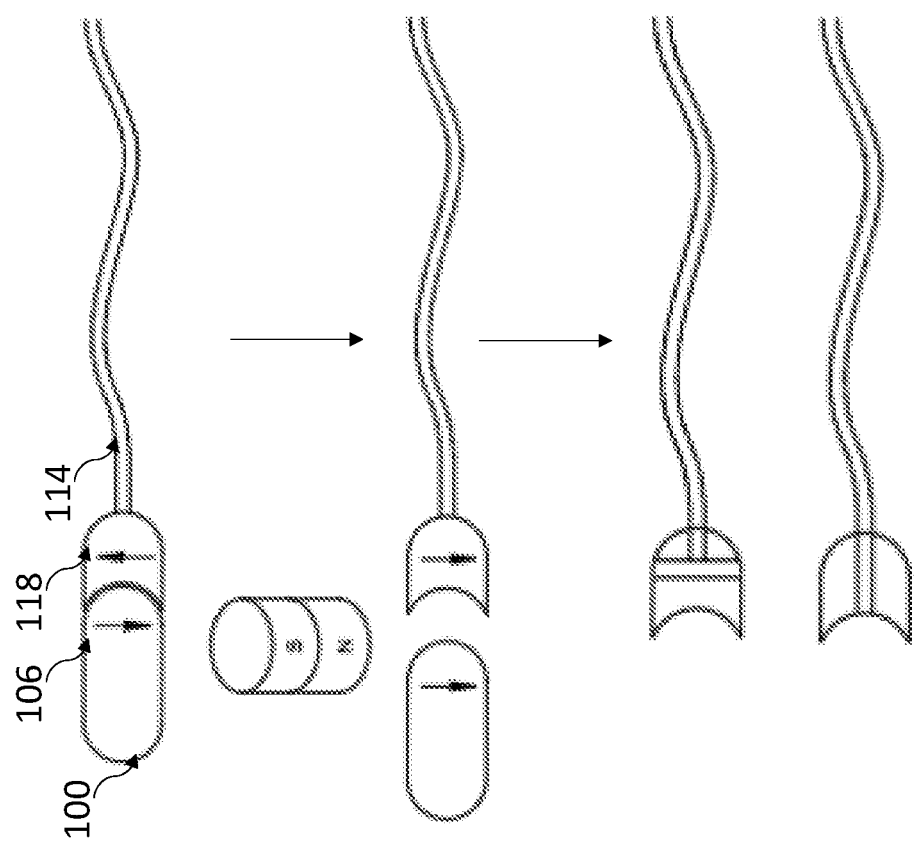
FIG. 28 is a schematic illustration of a magnetically releasable connection between a tether and an in-vivo capsule endoscope, according to an embodiment of the invention.

Reference is made to FIG. 28, which schematically illustrates a magnetically releasable connection between tether 110 and in-vivo capsule endoscope 100, according to an embodiment of the invention. Tether 110 may have a magnetically releasable end 118 fitted and connected to an end 106 of capsule endoscope 100. Magnetically releasable tether end 118 may have one or more invertible magnets having an invertible magnetic dipole oriented in a first direction at rest (absent a non-constant external magnetic field) (see e.g., up-arrow in the top image of FIG. 28). Capsule endoscope 100 has a permanent magnet 124 having a permanent magnetic dipole oriented in a second fixed direction (see e.g., down-arrow in the top image of FIG. 28). Tether's 110 first magnetic dipole direction may be substantially opposite (and equal) to capsule's 100 second magnetic dipole direction (absent an external magnetic field) to cause a magnetic attraction and connection between tether 110 and capsule endoscope 100. Tether's attachment end 118 may fit or inter-lock with capsule's attachment end 106, for example, by a concave/convex fitting (as shown in FIG. 28), flat fitting, lock and key fitting, or other fitting.

Tether 110 may be magnetically released from capsule endoscope 100 by exposure to an externally generated magnetic field (e.g., generated by the external magnetic control system of FIG. 5 or by a hand-held magnet sufficiently close to the capsule endoscope) that flips or inverts tether's invertible magnet so that its first magnetic dipole direction inverts (see e.g., up-arrow in top image flipped to down-arrow in second image in FIG. 28). Tether's inverted first magnetic dipole direction now aligns with the capsule's first magnetic dipole direction. This causes a repulsive magnetic force between magnets in capsule's end 106 and tether's end 118 so that the tether and capsule repel each other and separate.

In some embodiments, before or after the capsule is detached, tether 110 may inject or expel liquid into the organism's body. In one embodiment, tether 110 may collect samples of body fluids e.g., by drawing liquid via suction from the organism. In some cavities (e.g., the small bowel), too much or too little material makes it difficult for capsule endoscope 100 to move. Accordingly, inflation device may inject liquid (e.g., water or saline) or air via tether 110 into the cavity to inflate the cavity. Once inflated, the capsule may have more space for a better field of view, and/or reduced friction to make magnetic guidance easier.

Figure 29:
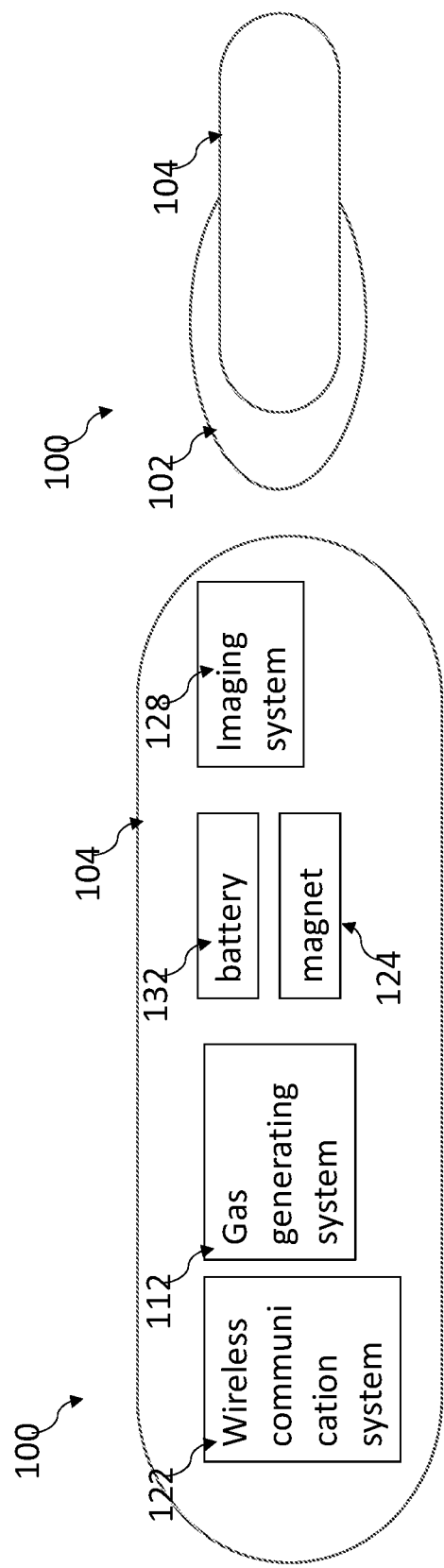
FIG. 29 is a schematic illustration of an autonomous (untethered) capsule endoscope comprising an in-vivo buoy and an in-vivo inflation device, according to an embodiment of the invention.

Reference is made to FIG. 29, which schematically illustrates an autonomous (untethered) system comprising an in-vivo buoy 102 and an in-vivo inflation device 112, according to an embodiment of the invention. In the autonomous system, inflation device 112 may be a part of, permanently attached to, or integral to, in-vivo capsule endoscope 100. Inflation device 112 may be positioned in-vivo or inside of the organism with the inflatable buoy 102 during inflation. In-vivo inflation device 112 may autonomously activate an in-vivo chemical reaction to generate and emit gas that inflates buoy 102 (e.g., without direct physical or manual contact with, or gas originating from, outside of the organism). In some embodiment, in-vivo inflation device 112 may be remotely activated to inflate/deflate buoy 102 via wireless communication system 122. Additionally or alternatively, in-vivo inflation device 112 may be locally activated in response to capsule 100 detecting one or more time/environment/imager conditions, such that in-vivo capsule endoscope 100 is autonomous and self-inflating and/or self-deflating (without remote control). In-vivo inflation device 112 may be an air compressor, chemical gas reactor, or gas powder to mix with water. In various embodiments, in-vivo inflation device 112 may be housed interior to the capsule-shaped body 104 (e.g., as shown in FIG. 29) or exterior to the capsule-shaped body 104 (e.g., inside or physically attached to buoy 102). In some embodiments in which inflation device 112 is housed interior to the capsule body 104, the capsule body 104 may have a (re-sealable) hole or channel 120 to transport gas from the internal inflation device 112 to the external inflation buoy 102, e.g., as shown in FIGS. 30 and 32. In some embodiments, in which inflation device 112 is housed exterior to the capsule body 104, the inflation device is affixed to the inflation buoy 102 itself.

Reference is made to FIGS. 33-43, which schematically illustrate an inflatable in-vivo capsule endoscope that is bi-directional with a dual-camera or two-sided imager to capture images in either forward and/or reverse axial direction, according to various embodiments of the invention.

Figure 33:
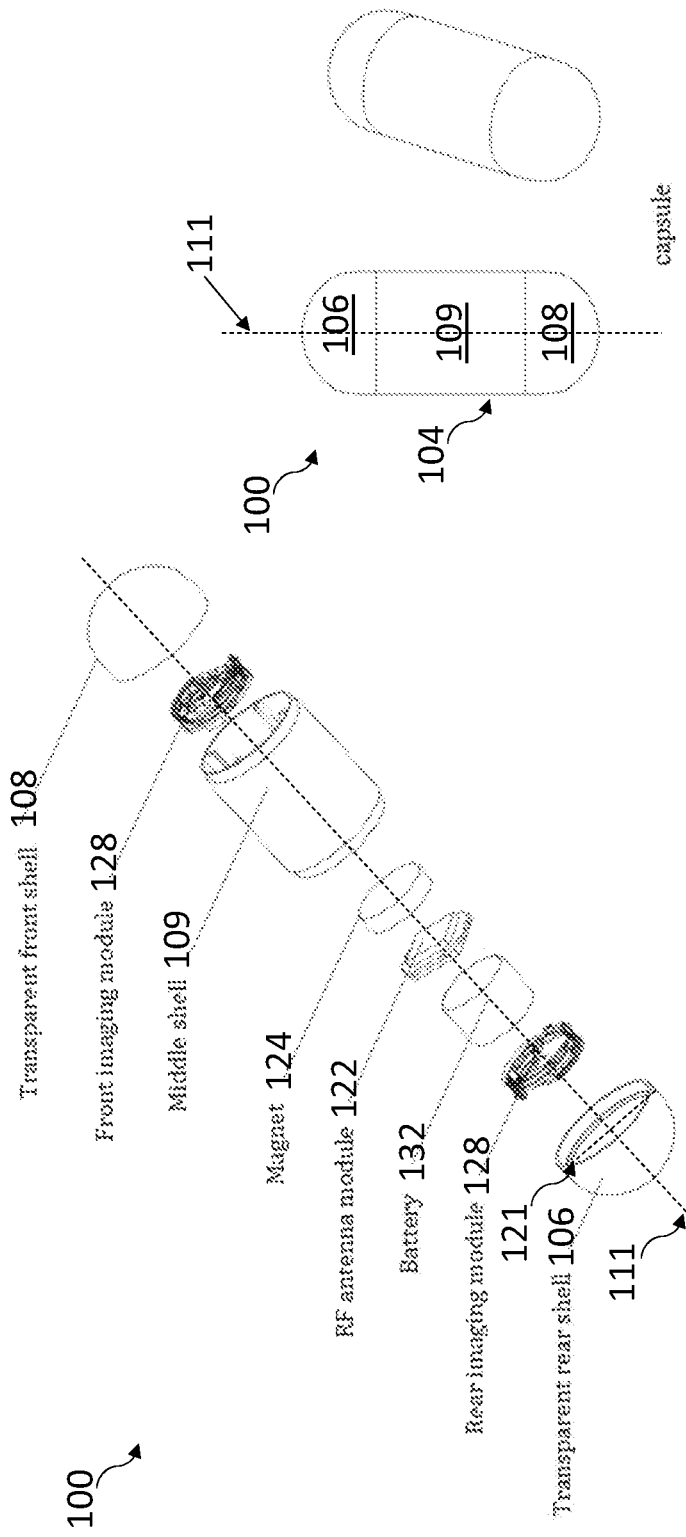
FIG. 33 is a schematic illustration of an exploded view of a bi-directional in-vivo capsule endoscope with a two-sided sensing device, according to an embodiment of the invention.

Reference is made to FIG. 33, which schematically illustrates an exploded view of a bi-directional in-vivo capsule endoscope 100 with a two-sided sensing device 128, e.g., housed internal to capsule-shaped body 104, according to an embodiment of the invention. Capsule-shaped body 104 may have a longitudinal axis 111 along its longest length and a radial axis 121 along a diameter of its circular cross-section. Capsule-shaped body 104 may have two concave end shells or hemispheres 106 and 108 at opposite ends of its longitudinal axis 111, and a middle (e.g., cylindrical-shaped) shell 109 joining end shells 106 and 108 at the center of its longitudinal axis 111. As capsule endoscope 100 is bi-directional, it has a dual or two-sided imager or sensing device 128 at opposite ends of its longitudinal axis 111 to capture images in either forward and/or reverse directions along its longitudinal axis 111. Both end shells 106 and 108 comprise transparent windows for housing the two sensing devices 128. Bi-directional capsule endoscope 100 may comprise other components as described in reference to FIGS. 4 and/or 22.

Reference is made to FIGS. 34-38 and 40-43, which are schematic illustrations of an in-vivo buoy 102 adapted to encapsulate a bi-directional in-vivo capsule endoscope 100, according to various embodiments of the invention. To encapsulate a bi-directional in-vivo capsule endoscope 100, in-vivo buoy 102 may not cover (or may transparently cover) the two opposite longitudinal end shells or hemispheres 106 or 108 of the endoscope 100. Since buoy 102 does not obscure either end, the two sensing devices 128 of bi-directional endoscope 100 have unobstructed fields of view (FOV), e.g., as shown in reference to FIGS. 36 and 38. Bi-directional endoscope buoy 102 may have various sizes and shapes, such as, torus-shaped (when inflated) and cylindrical-shaped (when deflated), spherical, ellipsoidal, etc.

In FIGS. 34-38, bi-directional endoscope buoy 102 is connected via an elongated tether 110 to an external inflation device 112.

Figure 34:
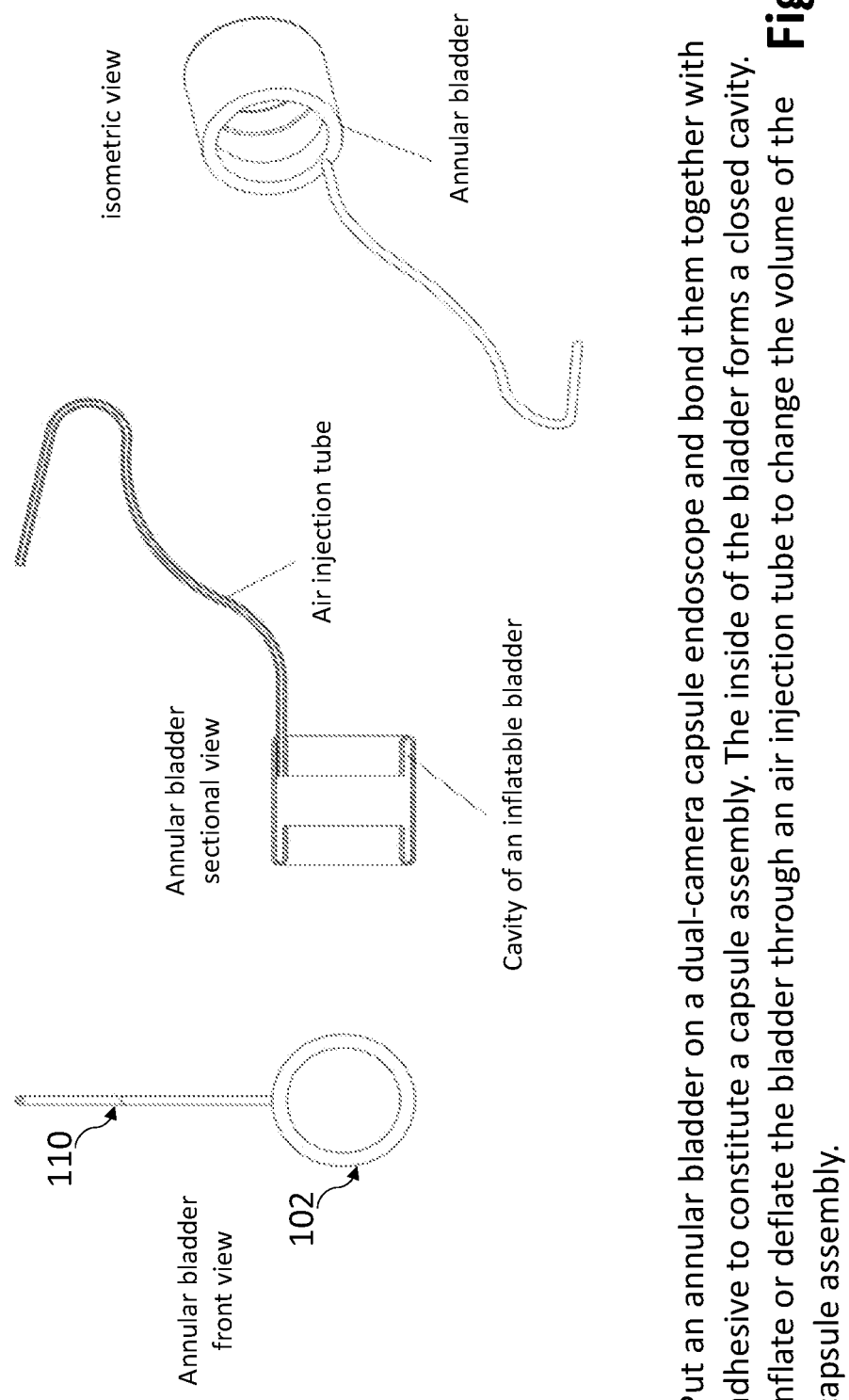
FIG. 34 is a schematic illustration of a tethered in-vivo buoy to inflate the bi-directional in-vivo capsule endoscope via an ex-vivo inflation device, according to an embodiment of the invention.
Figure 35:
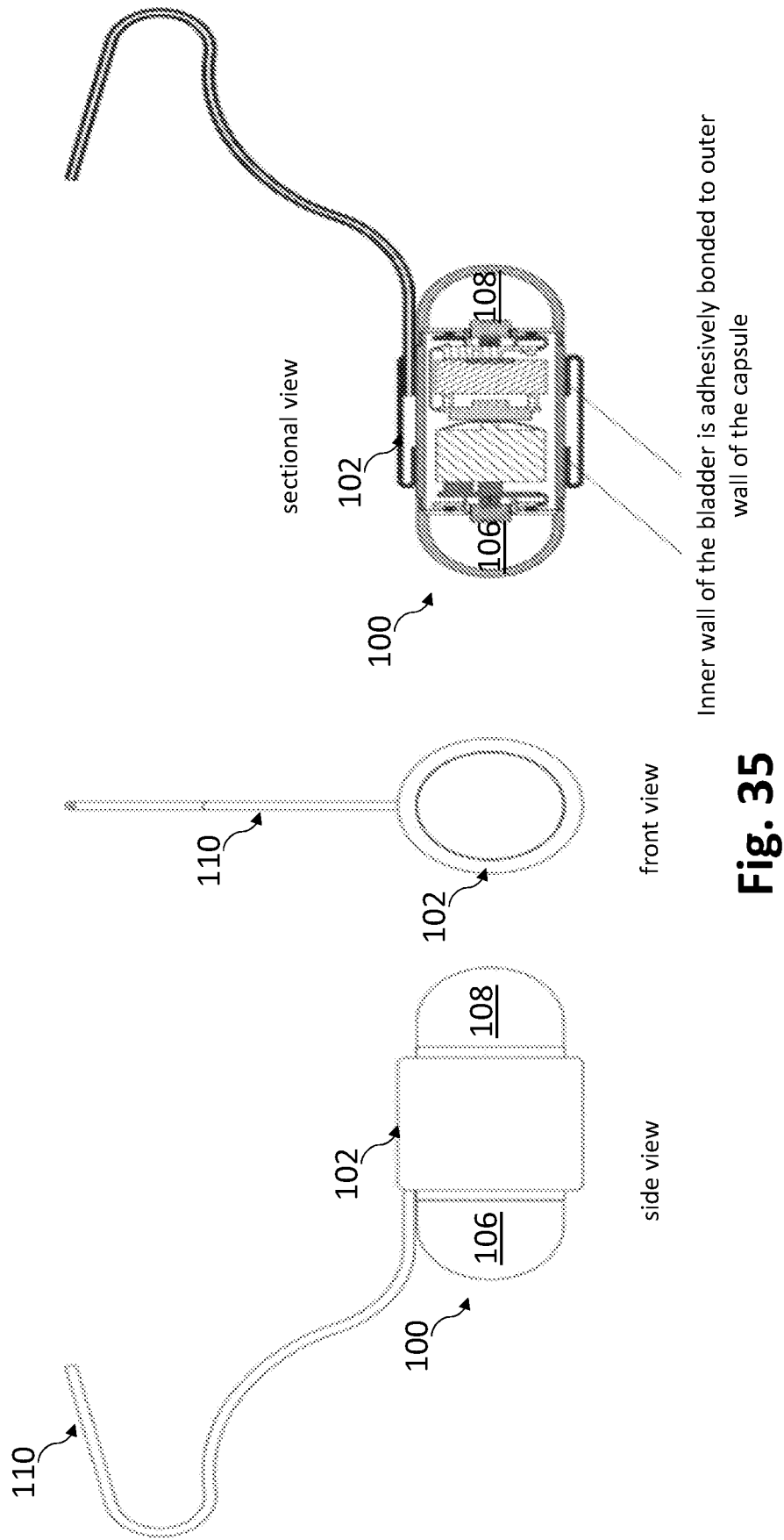
FIG. 35 is a schematic illustration of an uninflated tethered in-vivo buoy encapsulating the center trunk of the bi-directional in-vivo capsule endoscope, according to an embodiment of the invention.
Figure 36:
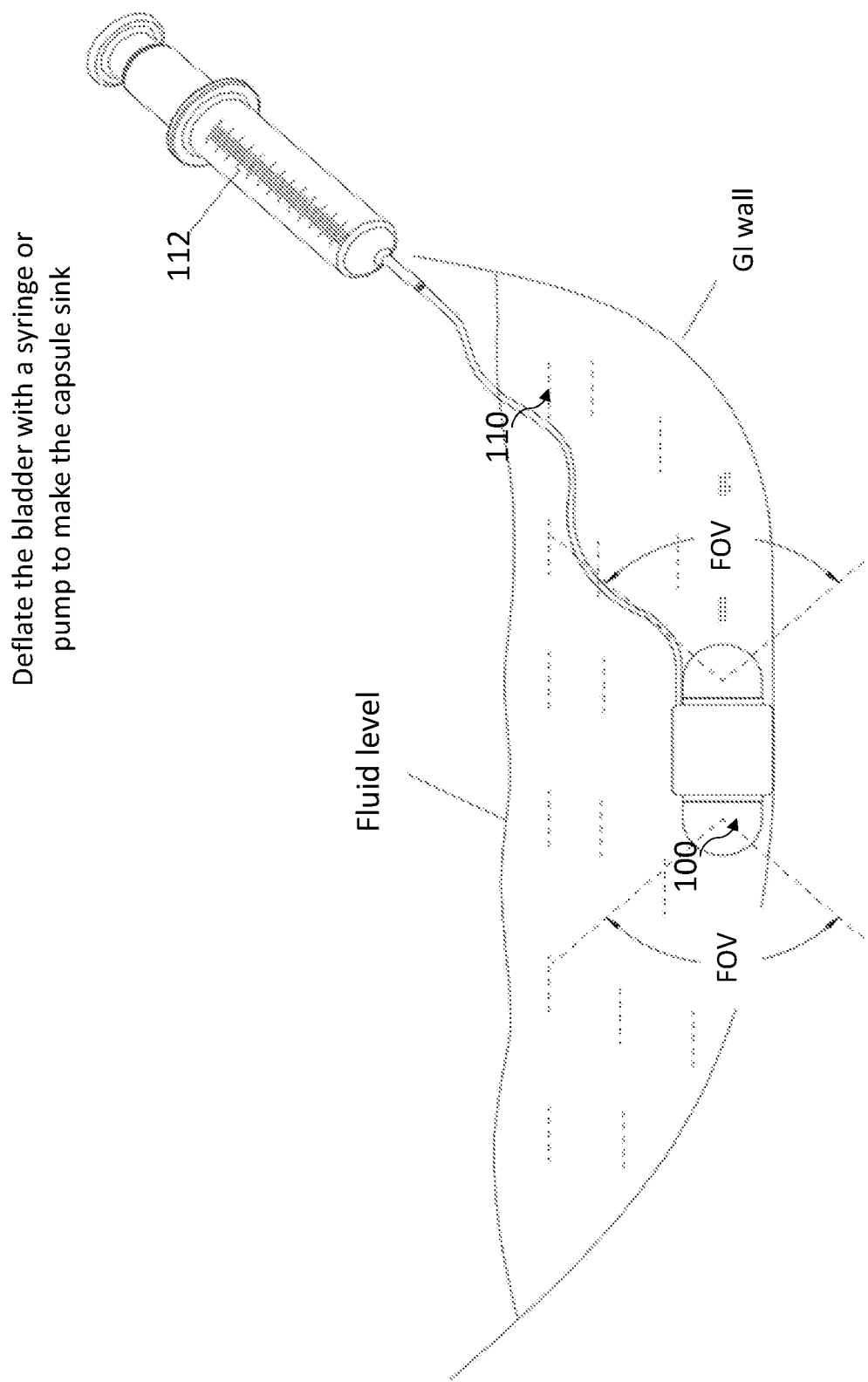
FIG. 36 is a schematic illustration of an inflatable bi-directional in-vivo capsule endoscope encapsulated by the tethered in-vivo buoy in a cavity of an organism in an uninflated state, according to an embodiment of the invention.

In FIG. 34, the bi-directional endoscope buoy 102 is connected to the tether 110, and in FIG. 35, the tethered assembly 102 and 110 encapsulates the center trunk (middle shell 109) of the bi-directional in-vivo capsule endoscope 100.

Figure 37:
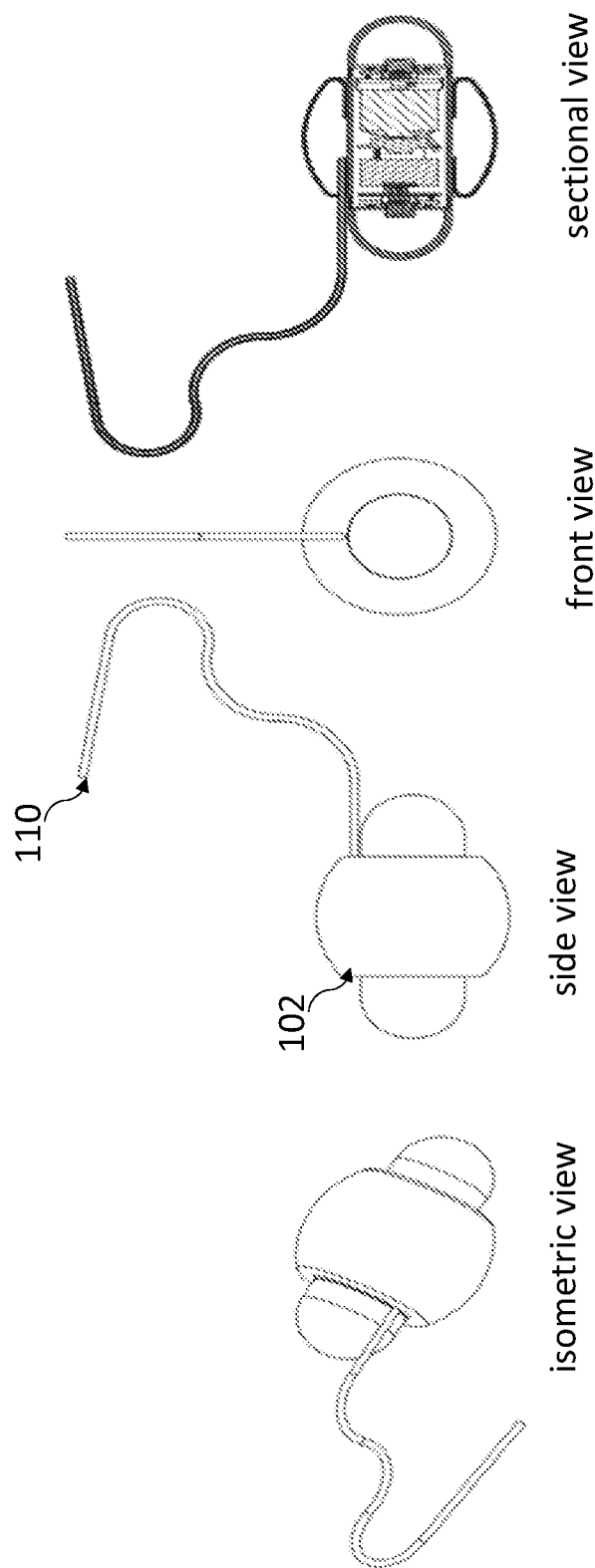
FIG. 37 is a schematic illustration of an inflated tethered in-vivo buoy encapsulating the center trunk of the bi-directional in-vivo capsule endoscope, according to an embodiment of the invention.
Figure 38:
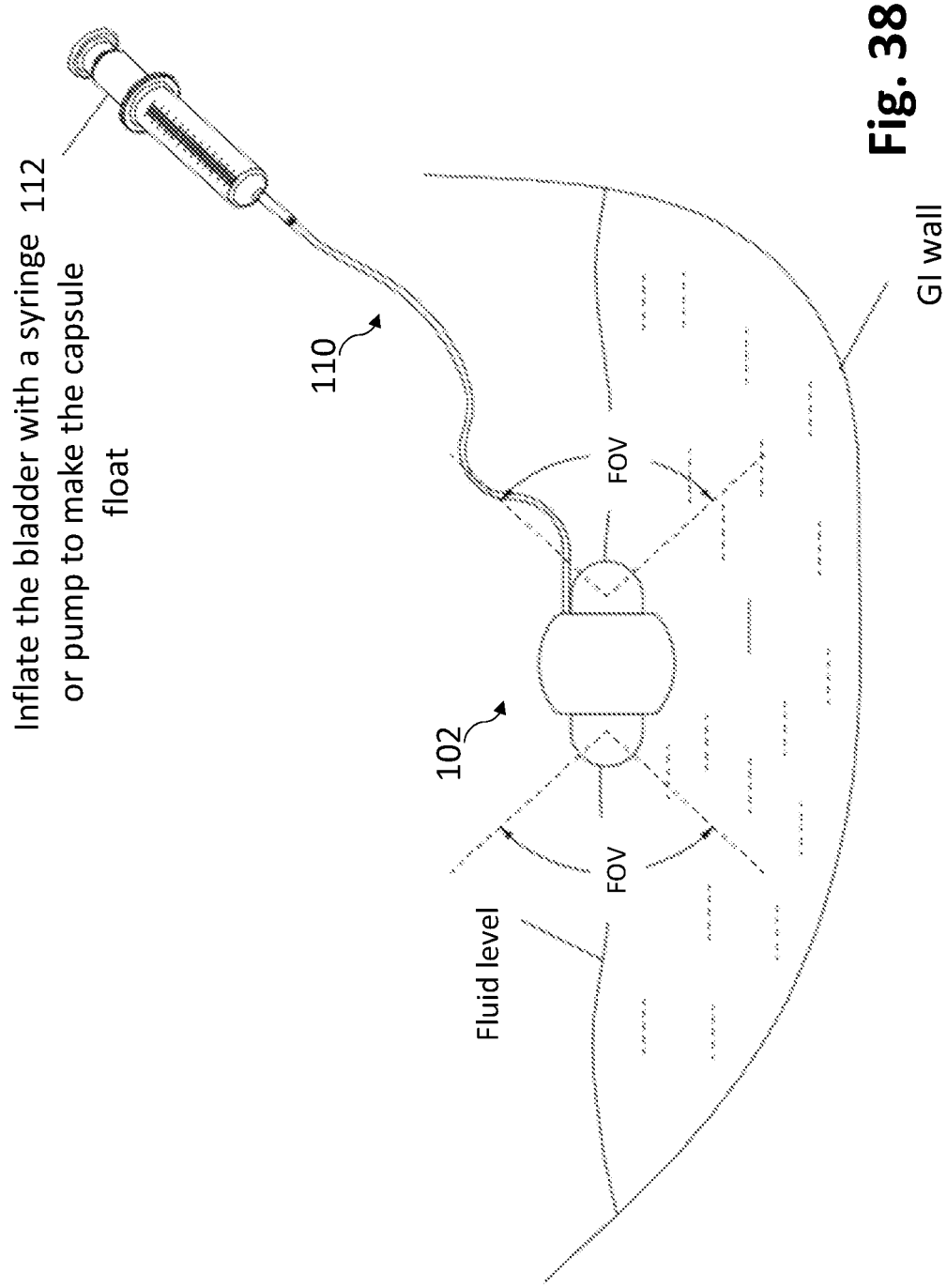
FIG. 38 is a schematic illustration of an inflatable bi-directional in-vivo capsule endoscope encapsulated by the tethered in-vivo buoy in a cavity of an organism in an inflated state, according to an embodiment of the invention.

The inflatable bi-directional in-vivo capsule endoscope 100 encapsulated by the tethered in-vivo buoy 102 is positioned in a cavity of an organism in an uninflated state (FIGS. 34-36) and in an inflated state (FIGS. 37-38). The inflation device 112 may inject liquid (e.g., water or saline) or air via tether 110 into the cavity of buoy 102 to inflate the cavity. Once inflated in FIG. 38, the capsule 100 may float above the cavity floor, to reduce or eliminate obstructions or occlusions by the cavity walls or floor to one or both of the two sensing devices of the bi-directional endoscope. Accordingly, the sensing devices may have better fields of view (FOV).

In FIGS. 39-43, bi-directional endoscope is autonomous (untethered) and contains an internal inflation device 112 to inflate buoy 102.

Figure 39:
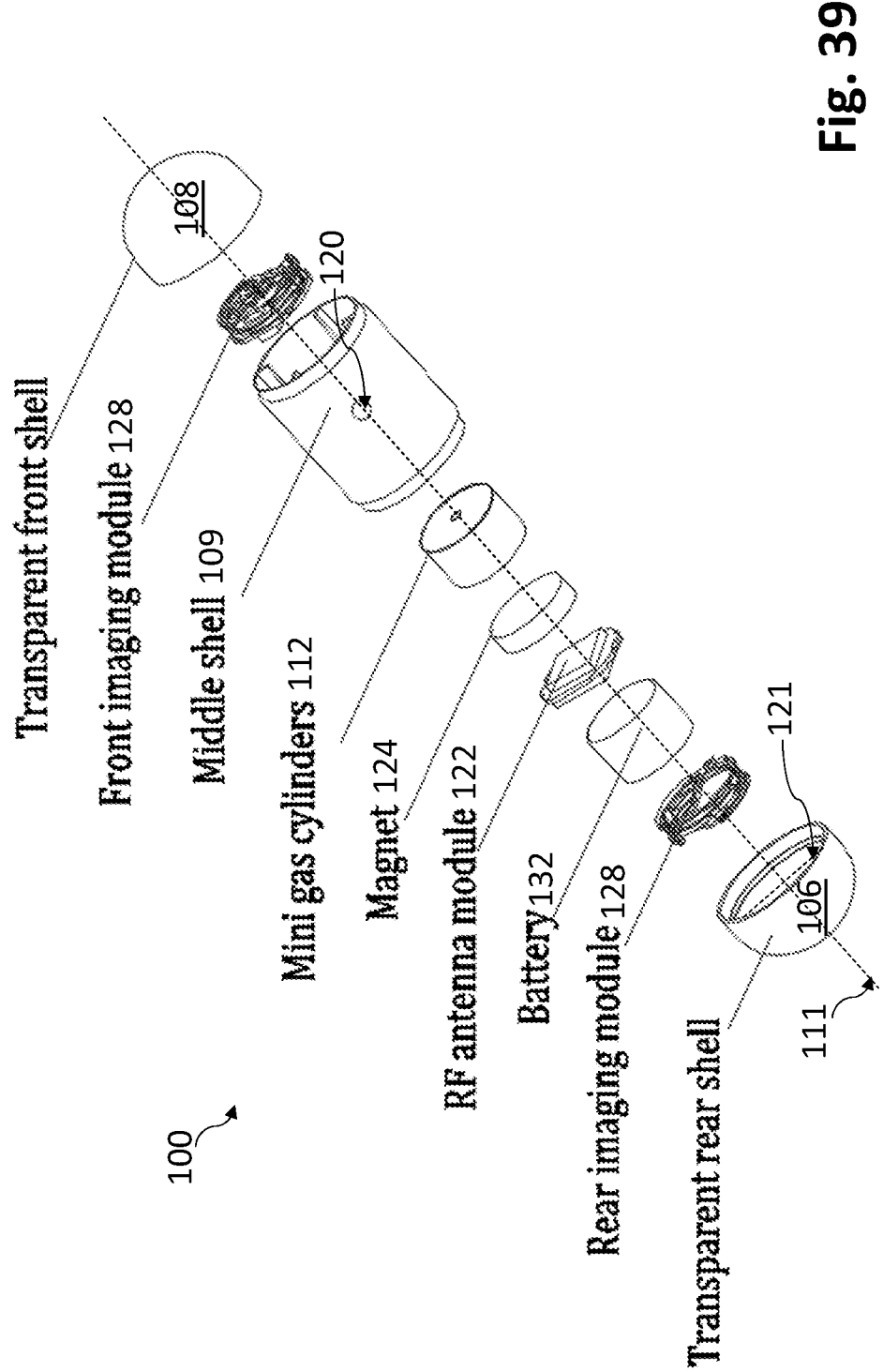
FIG. 39 is a schematic illustration of an exploded view of an autonomous (untethered) bi-directional in-vivo capsule endoscope comprising an internal inflation device and a hole for transporting gas to an external inflation buoy, according to an embodiment of the invention.

Reference is made to FIG. 39, which schematically illustrates an exploded view of an autonomous (untethered) bi-directional in-vivo capsule endoscope 100 comprising an internal inflation device 112, according to an embodiment of the invention. In the autonomous system, inflation device 112 may be a part of, permanently attached to, or integral to, in-vivo capsule endoscope 100 and may operate as described in reference to FIGS. 29-32. Inflation device 112 may be positioned in-vivo or inside of the organism with the inflatable buoy 102 during inflation. In-vivo inflation device 112 may autonomously activate an in-vivo chemical reaction to generate and emit gas that inflates buoy 102. In some embodiments, gas generated by interior inflation device 112 is transported via a (re-sealable) hole or channel 120 to inflate inflation buoy 102, e.g., as shown in FIGS. 41 and 43.

Figure 40:
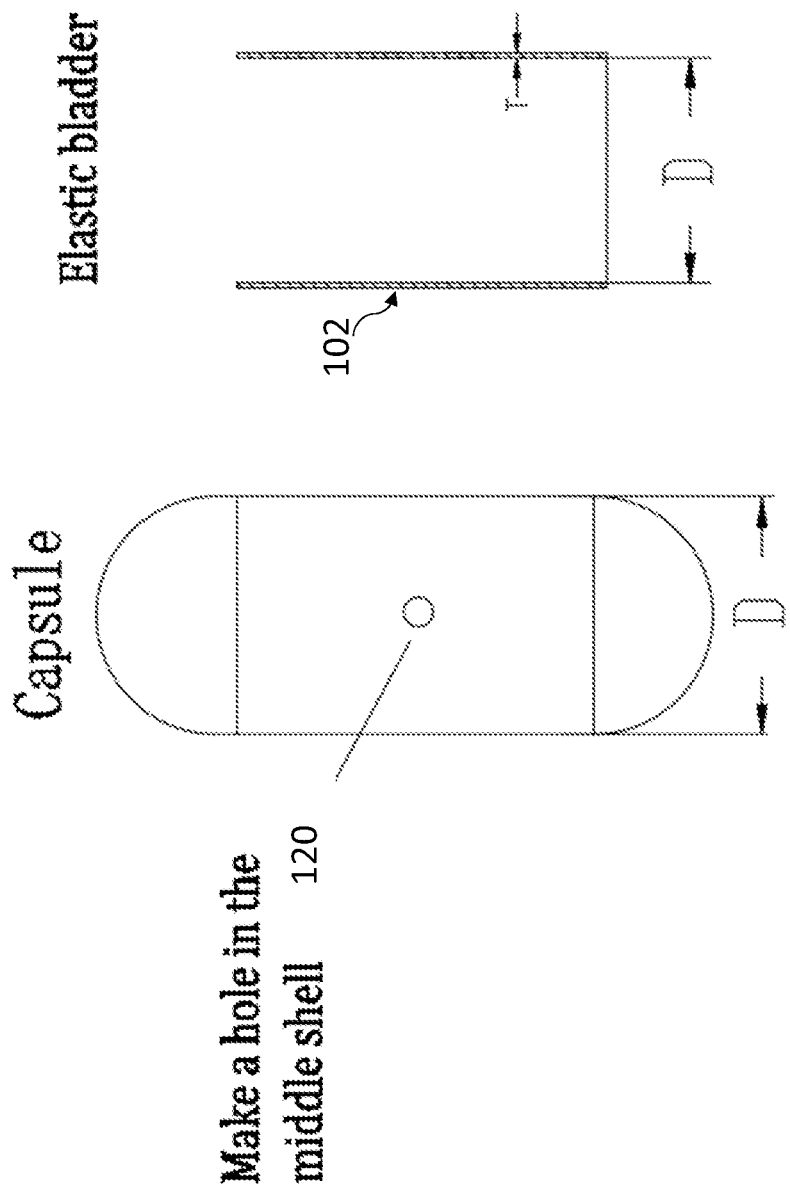

Reference is made to FIGS. 40-41, which schematically illustrate the autonomous bi-directional in-vivo capsule endoscope that is inflatable by a "cup expansion" type buoy, according to an embodiment of the invention.

Figure 42:
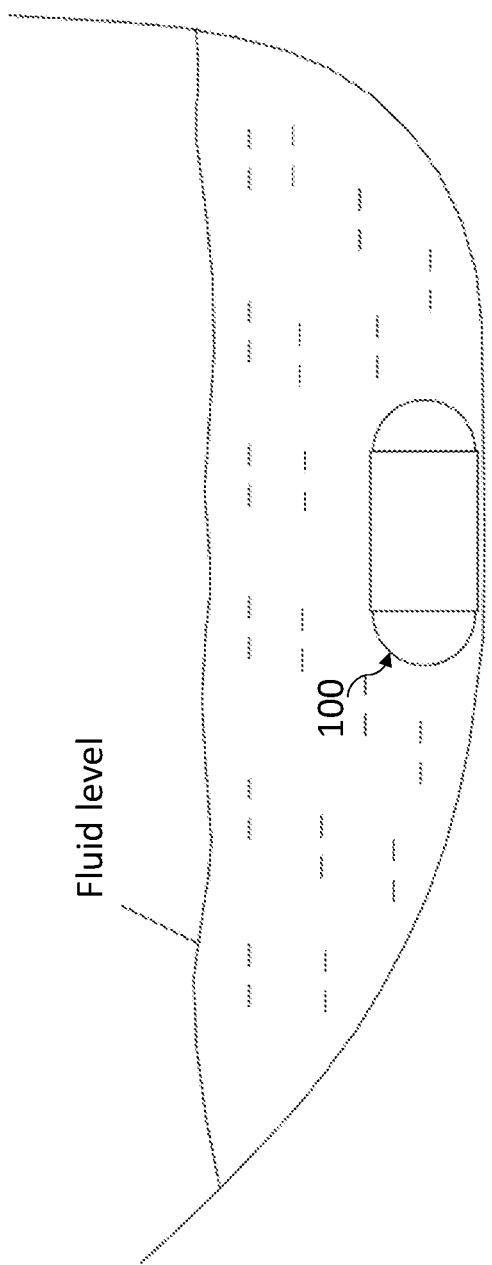
FIGS. 42 and 43 are schematic illustrations of the autonomous inflatable bi-directional in-vivo capsule endoscope in a cavity of an organism in an uninflated state (FIG. 42) and an inflated state (FIG. 43), according to an embodiment of the invention.
Figure 43:
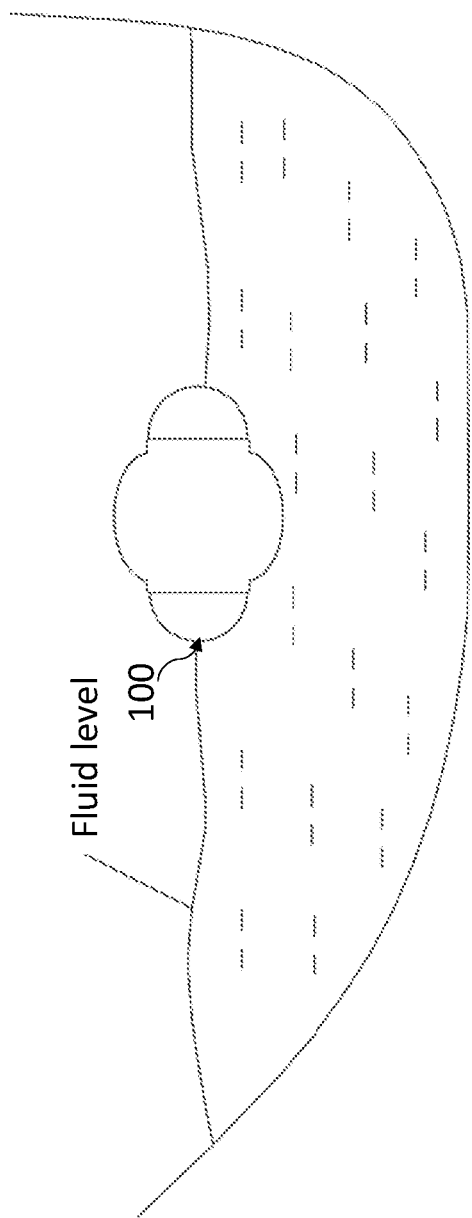

Reference is made to FIGS. 42 and 43, which schematically illustrate the autonomous inflatable bi-directional in-vivo capsule endoscope 100 in a cavity of an organism in an uninflated state (FIG. 42) and an inflated state (FIG. 43), according to an embodiment of the invention. The internal inflation device 112 may autonomously activate an in-vivo chemical reaction to generate and emit gas via a hole 120 into the cavity of buoy 102 to inflate the cavity. Once inflated in FIG. 42, the capsule 100 floats above the cavity floor, to reduce or eliminate obstructions and improve the visibility and effective field of view of one or both of the two sensing devices of the bi-directional endoscope 100.

Reference is made to FIG. 44, which is a flowchart of a method of operating an inflatable in-vivo capsule endoscope, according to an embodiment of the invention. The operations of FIG. 44 may be executed using the inflatable in-vivo capsule endoscope disclosed in reference to one or more of FIGS. 1-43.

In operation 1000, an inflatable in-vivo capsule endoscope (e.g., 100 of FIGS. 1-4, 6, 8, 10-18, 20-26, 28-33, and 35-43) may be introduced in an uninflated state into a cavity comprising liquid inside an organism (see e.g., FIG. 2). The capsule endoscope may comprise a capsule-shaped body (e.g., 104), an inflatable buoy (e.g., 102) external to the capsule-shaped body, and a sensing device (e.g., 128) for capturing in-vivo images housed interior to the capsule-shaped body.

In operation 1002, an inflation device (e.g., 112) may be activated to inflate the inflatable buoy by injecting an above threshold volume of gas into the inflatable buoy to reduce the specific gravity of the in-vivo capsule endoscope, such that, the inflatable in-vivo capsule endoscope floats in the liquid cavity. In one embodiment, the inflatable in-vivo capsule endoscope may float based only on buoyancy, e.g., by injecting a volume of gas such that the density of the in-vivo capsule endoscope is less than or equal to the density of water. In another embodiment, the inflatable in-vivo capsule endoscope may float based on a combination of injecting a volume of gas and magnetically lifting the capsule by exposure to an externally generated magnetic field. The inflation/deflation device may inject or expel gas to a desired volume or pressure to tune the floatation height level of the inflatable in-vivo capsule endoscope relative to the height level of the liquid.

In some embodiments, a tethered system may be used (see e.g., FIGS. 2-3, 6-21, 23-26, 28 and 34-38). In a tethered system, the inflation device may be an ex-vivo inflation device positioned outside of an organism when inflating the in-vivo inflatable buoy positioned inside of the organism. The ex-vivo inflation device may be attached to the buoy by an elongated tether (e.g., 110) that traverses at least a portion of the organism (see e.g., FIG. 6). The tether may be magnetically attached to or released from the capsule-shaped body (see e.g., FIG. 28). The tether may be used to draw liquid to collect body fluids from the organism.

In some embodiments, an autonomous (untethered) system may be used (see e.g., FIGS. 29-32 and 39-43). In an autonomous (untethered) system, the inflation device may be an in-vivo inflation device that is permanently attached to the capsule-shaped body and positioned inside of the organism with the inflatable buoy during inflation. The in-vivo inflation device may autonomously generate the gas by a chemical reaction in the in-vivo inflation device.

In some embodiment, the inflation buoy may be positioned asymmetrically relative to a radial axis of the capsule body, such that the capsule-shaped body is oriented by inflating the asymmetrically positioned inflation buoy (e.g., the buoy rises to the top) (see e.g., FIGS. 15-18). In one embodiment, the capsule-shaped body is oriented level with its longitudinal axis (see e.g., FIGS. 15-16). In another embodiment, the capsule-shaped body is oriented to direct the sensing device's field of view towards a targeted area (see e.g., FIGS. 17-18). In some embodiment, the capsule endoscope is bi-directional having two sensing devices oriented in opposite directions (see e.g., FIGS. 33-43).

In operation 1004, the floating in-vivo capsule endoscope may be magnetically navigated by exposing one or more permanent magnets (e.g., 124) housed interior to the capsule-shaped body having a permanent magnetic dipole moment to an externally generated magnetic field that magnetically guides the inflatable in-vivo capsule endoscope. An external magnetic control system (e.g., 126 of FIG. 5) may be operated to generate the magnetic field. The externally generated magnetic field may be operated at a significantly weaker intensity for magnetically guiding a capsule floating in liquid (e.g., approximately 75 A/cm$^2$), and thus may be generated using a significantly smaller external magnet, than is used to guide a conventional (uninflated) capsule (e.g., approximately 2500 A/cm$^2$).

In some embodiments, the inflation buoy has a corkscrew-shaped surface (see e.g., FIGS. 19-27) such that the inflatable in-vivo capsule endoscope rotates in a spiral motion when it is magnetically navigated thorough a channel. The inflatable in-vivo capsule endoscope may propel forward when the corkscrew-shaped surface rotates in a first direction and backwards when the corkscrew-shaped surface rotates in an opposite direction. The inflation buoy may be inflated to a diameter that substantially matches a channel diameter to achieve a target pressure between the endoscope and the channel. The in-vivo capsule endoscope may be magnetically rotated about its longitudinal axis to propel the corkscrew-shaped surface.

In operation 1006, an deflation device (e.g., 112 or another device) may be activated to deflate the inflatable buoy by expelling gas such that the inflatable in-vivo capsule endoscope sinks in the liquid cavity. Once the in-vivo capsule endoscope is partially or fully uninflated, it can be either retracted backwards through the esophagus via a tether or detached and guided forward to progress autonomously through the remainder of the GI tract.

A method is provided for manufacturing or assembling the components or parts of the inflatable in-vivo capsule endoscope 100 shown in FIGS. 1-4, 6, 8, 10-18, 20-26, 28-33 and/or 35-43.

Embodiments of the invention provide capsule endoscope 100 with an inflatable buoy 102 to examine areas of the GI tract, such as, the esophagus and stomach. Capsule endoscope may be tethered by an elongated tube, which may be volume adjustable and expandable by controlling the injection/disposal of gas. When the capsule endoscope is in liquid in a cavity, the volume adjustable expanded tube can provide an additional floating force to the capsule endoscope. Combined with the external magnetic control, the capsule endoscope is easier to move inside the water. While in channels, such as the small bowl, the volume adjustable buoy expands in a spiral-shaped structure to further move in esophagus or in small bowl by the aid of external magnetic control.

Buoy expansion can adjust the effective specific gravity of capsule in water thus changing the float force. This method can reduce the magnetic induction intensity requirement of external magnetic field during capsule inspection for position and orientation change of the capsule. The external magnetic field intensity used to control the capsule endoscope whose specific gravity is greater than water, is greater than the capsule whose specific gravity is less than or equal to water. The buoy membrane may be glued to form a bladder. The gravitational center location vs. the geometry center changes the posture of the capsule when the bladder is injected with air. This will help to achieve different angles of observation by injecting different amounts of air, as well as by magnetic guidance. After the digestive tract examination is completed, the air in the balloon may be withdrawn, so that the volume of the capsule body is minimized, and the entire capsule is pulled back from the mouth by the tether, or detached from the tether and allowed to proceed autonomously through the remainder of the digestive tract.

Although embodiments of the invention describe inflating a buoy external to the capsule body, the buoy may also be disposed internal to the capsule body or may be the capsule body itself, where the capsule body is expandable, elastic or deformable.

Although the application describes inflating the buoy with a gas, the buoy may also be inflated with other materials, such as, foam, oil, or other gaseous or liquid substances or mixtures that have a lower density than water. The matter may be supplied by the buoy itself, a reservoir internal to the capsule body via an internal channel, or may be absorbed from the capsule's ambient environment in the organism's cavity via an external channel.

The principles of the invention shown and described may also be applied to additional uses in vivo or to probes used in other contexts such as mechanical or fluid-handling systems. The term "capsule" may be used interchangeably with the term "probe" herein to refer to probe apparatus and similar remote objects in general, regardless of shape. It should be understood that a capsule may be spherical, ellipsoidal, cylindrical with two half-domes, or other suitable shapes or combinations of shapes. In FIG. 1, the magnetic capsule has a length, which is the longest dimension of the capsule. The length direction is referred as a longitude direction or axis 111 of the capsule. The magnetic capsule does not have to have a cylinder shape having one or two half domed ends as shown in FIG. 1. The capsule can be of any shape and weight as long as the fundamental physical principal is applicable to the magnetic capsule.

The capsule has a magnetic dipole direction, which is parallel to the capsule longitudinal axis 111, either forward or backward. The capsule may thus be magnetically guided to move linearly, such that, the movement direction is the same as, coincide, or parallel as the longitude direction of the capsule. In some embodiments, the capsule has a magnetic dipole direction that is asymmetrical relative to its radial axis 121, which together or separate from the spiral exterior surface or buoy, causes the capsule to be magnetically guided to rotate about its longitudinal axis, thereby moving in a spiral or a corkscrew motion. This corkscrew motion may aid in propulsion forwards or backwards, e.g., through channels of the GI tract. The capsule moves forward may mean that the capsule progresses along the tract farther away from the mouth or entry point. The capsule moves backward may mean that the capsule moves along the tract towards and closer to the mouth or entry point. The front end, in one example, comprising a diagnostic sensor or therapeutic device, such as a camera. The back end, which may be linearly opposite to the front end, can also include a complimentary diagnostic sensor or therapeutic device, or may simply comprise a shell.

Although capsule endoscope is shown to be located in specific cavities, such as, a stomach in FIGS. 2 and 3, this is only an example, and any other cavity or organism may be used.

For simplicity purpose, capsule endoscope 100 is described in the context of biomedical applications, i.e. the target location is an in vivo location, for example a location inside a digestive tract. For simplicity purpose, the medical device disclosed herein is designed to be placed in vivo. One of the non-invasive methods of delivery is by swallow into a digestive tract. Therefore, the medical device disclosed herein is referred as a capsule, which should not be construed as a limitation for its shape, dimension or size. The capsule device disclosed herein and methods of using the same can be implemented for many other applications beyond biomedical applications.

Various embodiments of the invention include:
1. An inflatable in-vivo capsule endoscope comprising:
   a capsule-shaped body;
   a sensing device for capturing in-vivo images housed interior to the capsule-shaped body;
   an inflatable buoy external to the capsule-shaped body;
   an inflation device configured to inflate the in-vivo capsule endoscope by injecting gas into the inflatable buoy to reduce the specific gravity of the in-vivo capsule endoscope, such that when the inflatable buoy is injected with an above threshold volume of gas, the inflatable in-vivo capsule endoscope is configured to float in liquid; and
   one or more permanent magnets housed interior to the capsule-shaped body having a permanent magnetic moment for magnetically guiding the inflatable in-vivo capsule endoscope when exposed to an externally generated magnetic field.
2. The inflatable in-vivo capsule endoscope of 1, wherein the inflation device injects a volume of gas such that the density of the in-vivo capsule endoscope is less than or equal to the density of water.
3. The inflatable in-vivo capsule endoscope of 1, wherein the inflation device injects a volume of gas such that the density of the in-vivo capsule endoscope is greater than the density of water by an amount counteracted by a magnetic lift force.
4. The inflatable in-vivo capsule endoscope of 1, comprising a deflation device configured to increase the specific gravity of the in-vivo capsule endoscope by expelling gas, such that when the inflatable buoy has a below threshold volume of gas, the inflatable in-vivo capsule endoscope sinks in liquid.
5. The inflatable in-vivo capsule endoscope of 1, wherein the inflation device injects or expels gas to a desired volume or pressure to tune the floatation height level of the inflatable in-vivo capsule endoscope relative to the height level of the liquid.
6. The inflatable in-vivo capsule endoscope of 1, wherein the inflation buoy has a corkscrew-shaped surface when inflated to propel the inflatable in-vivo capsule endoscope forward by rotating in a spiral motion.

7. The inflatable in-vivo capsule endoscope of 6, wherein the corkscrew-shaped surface propels the inflatable in-vivo capsule endoscope forward when rotating in a first direction and backwards when rotating in an opposite direction.

8. The inflatable in-vivo capsule endoscope of 6, wherein the inflation device inflates the inflation buoy to a diameter that substantially matches a channel diameter to achieve a target pressure between the endoscope and the channel to propel the endoscope regardless of channel diameter.

9. The inflatable in-vivo capsule endoscope of 6, wherein the permanent magnets are radially spaced from the center of mass with respect to a radial axis of the capsule-shaped body to cause an asymmetric spiraling force for propelling the corkscrew-shaped surface when exposed to the externally generated magnetic field.

10. The inflatable in-vivo capsule endoscope of 1, wherein the inflation device is an ex-vivo device that is positioned outside of an organism when inflating the in-vivo inflatable buoy positioned inside of the organism.

11. The inflatable in-vivo capsule endoscope of 10, wherein the ex-vivo inflation device is attached to the buoy by an elongated tether that traverses at least a portion of the GI tract of the organism.

12. The inflatable in-vivo capsule endoscope of 11, wherein the tether is magnetically attached to the capsule-shaped body.

13. The inflatable in-vivo capsule endoscope of 12, wherein the tether is magnetically separable from the capsule-shaped body by exposure to an externally generated magnetic field causing a repulsive magnetic force between magnets in the tether and the capsule-shaped body.

14. The inflatable in-vivo capsule endoscope of 10, wherein the external inflation device is a syringe.

15. The inflatable in-vivo capsule endoscope of 10, wherein the external inflation device is a pump.

16. The inflatable in-vivo capsule endoscope of 10, wherein the tether is configured to draw liquid for collecting body fluids from the organism.

17. The inflatable in-vivo capsule endoscope of 1, wherein the inflation device is an in-vivo device permanently attached to the capsule-shaped body that is positioned inside of the organism with the inflatable buoy during inflation.

18. The inflatable in-vivo capsule endoscope of 17, wherein the inflation device autonomously generates the gas by a chemical reaction.

19. The inflatable in-vivo capsule endoscope of 17, wherein the in-vivo inflation device is housed interior to the capsule-shaped body and the body has a hole to transport the gas from the internal inflation device to the external inflation buoy.

20. The inflatable in-vivo capsule endoscope of 17, wherein the inflation device is affixed to the inflation buoy external to the capsule-shaped body.

21. The inflatable in-vivo capsule endoscope of 17, wherein the inflation buoy is positioned asymmetrically relative to a radial axis of the capsule body, such that the inflation buoy rises to a relatively higher liquid level to rotationally orient the capsule-shaped body.

22. The inflatable in-vivo capsule endoscope of 1, comprising an external magnetic control system to generate the externally generated magnetic field.

23. The inflatable in-vivo capsule endoscope of 1, wherein the inflatable buoy encapsulated the portion of the capsule-shaped body outside of the field of view of the sensing device.

24. The inflatable in-vivo capsule endoscope of 1 comprising a one-sided sensing device encapsulated by a concave inner surface of the inflation buoy.

25. The inflatable in-vivo capsule endoscope of 1 comprising a two-sided sensing device encapsulated by a cylindrical inner surface of the inflation buoy.

26. A method of operating an inflatable in-vivo capsule endoscope, the method comprising:
   introducing an inflatable in-vivo capsule endoscope in an uninflated state into a cavity comprising liquid inside an organism, said capsule endoscope comprising a capsule-shaped body, an inflatable buoy external to the capsule-shaped body, and a sensing device for capturing in-vivo images housed interior to the capsule-shaped body;
   activating an inflation device to inflate the inflatable buoy by injecting an above threshold volume of gas into the inflatable buoy to reduce the specific gravity of the in-vivo capsule endoscope, such that, the inflatable in-vivo capsule endoscope floats in the liquid cavity; and
   magnetically navigating the floating in-vivo capsule endoscope by exposing one or more permanent magnets housed interior to the capsule-shaped body having a permanent magnetic dipole moment to an externally generated magnetic field that magnetically guides the inflatable in-vivo capsule endoscope.

27. The method of 26 comprising causing the inflatable in-vivo capsule endoscope to float by injecting a volume of gas such that the density of the in-vivo capsule endoscope is less than or equal to the density of water.

28. The method of 26 comprising causing the inflatable in-vivo capsule endoscope to float by a combination of injecting a volume of gas and magnetically lifting the capsule by exposure to an externally generated magnetic field.

29. The method of 26 comprising deflating the inflatable buoy by expelling gas such that the inflatable in-vivo capsule endoscope sinks in liquid.

30. The method of 26 comprising injecting or expelling gas to a desired volume or pressure to tune the floatation height level of the inflatable in-vivo capsule endoscope relative to the height level of the liquid.

31. The method of 26, wherein the inflation buoy has a corkscrew-shaped surface such that the inflatable in-vivo capsule endoscope rotates in a spiral motion when it is magnetically navigated thorough a channel.

32. The method of 31 comprising propelling the inflatable in-vivo capsule endoscope forward when the corkscrew-shaped surface rotates in a first direction and backwards when the corkscrew-shaped surface rotates in an opposite direction.

33. The method of 31 comprising inflating the inflation buoy to a diameter that substantially matches a channel diameter to achieve a target pressure between the endoscope and the channel.

34. The method of 31 comprising magnetically rotating the in-vivo capsule endoscope about its longitudinal axis to propel the corkscrew-shaped surface.

35. The method of 26 comprising activating an ex-vivo inflation device positioned outside of an organism when inflating the in-vivo inflatable buoy positioned inside of the organism, wherein the ex-vivo inflation device is attached to the buoy by an elongated tether that traverses at least a portion of the organism.

36. The method of 35 comprising magnetically attaching or releasing the tether to or from the capsule-shaped body.

37. The method of 35 comprising drawing liquid through the tether to collect body fluids from the organism.

38. The method of 26 comprising activating an in-vivo inflation device that is permanently attached to the capsule-shaped body and positioned inside of the organism with the inflatable buoy during inflation.

39. The method of 38 comprising autonomously generating the gas by a chemical reaction in the in-vivo inflation device.

40. The method of 26, wherein the inflation buoy is positioned asymmetrically relative to a radial axis of the capsule body, comprising orienting the capsule-shaped body by inflating the asymmetrically positioned inflation buoy.

41. The method of 26 comprising generating the externally generated magnetic field by operating an external magnetic control system.

42. A method of manufacturing the inflatable in-vivo capsule endoscope of any of 1-25.

In the foregoing description, various aspects of the present invention are described. For purposes of explanation, specific configurations and details are set forth in order to provide a thorough understanding of the present invention. However, it will also be apparent to persons of ordinary skill in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

The aforementioned flowchart and block diagrams illustrate the architecture, functionality, and operation of possible implementations of systems and methods according to various embodiments of the present invention. In this regard, each block in the flowchart or block diagrams may represent a module, segment, or portion of code, which may comprise one or more executable instructions for implementing the specified logical function(s). In some alternative implementations, the functions noted in the block may occur out of the order noted in the figures or by different modules. Unless explicitly stated, the method embodiments described herein are not constrained to a particular order or sequence. Additionally, some of the described method embodiments or elements thereof can occur or be performed at the same point in time. Each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Embodiments of the invention may include an article such as a non-transitory computer or processor readable medium, or a computer or processor non-transitory storage medium, such as for example a memory (e.g., memory units of processing board(s) in FIG. 4), a disk drive, or a USB flash memory, encoding, including or storing instructions, e.g., computer-executable instructions, which, when executed by a processor or controller (e.g., processing board(s) in FIG. 4), carry out methods disclosed herein.

In the above description, an embodiment is an example or implementation of the inventions. The various appearances of "one embodiment," "an embodiment" or "some embodiments" do not necessarily all refer to the same embodiments. Although various features of the invention may be described in the context of a single embodiment, the features of embodiments may also be provided separately or in any suitable combination. Conversely, although the invention may be described herein in the context of separate embodiments for clarity, the invention may also be implemented in a single embodiment. Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions. It will further be recognized that the aspects of the invention described hereinabove may be combined or otherwise coexist in embodiments of the invention.

The descriptions, examples, methods and materials presented in the claims and the specification are not to be construed as limiting but rather as illustrative only. While certain features of the present invention have been illustrated and described herein, many modifications, substitutions, changes, and equivalents may occur to those of ordinary skill in the art. It is, therefore, to be understood that the appended claims are intended to cover all such modifications and changes as fall with the true spirit of the invention.

While the invention has been described with respect to a limited number of embodiments, these should not be construed as limitations on the scope of the invention, but rather as exemplifications of some of the preferred embodiments. Other possible variations, modifications, and applications are also within the scope of the invention. Different embodiments are disclosed herein. Features of certain embodiments may be combined with features of other embodiments; thus certain embodiments may be combinations of features of multiple embodiments. Accordingly, the scope of the invention should not be limited by what has thus far been described, but by the appended claims and their legal equivalents.

The invention claimed is:

1. A method of operating an inflatable in-vivo capsule endoscope, the method comprising:
   introducing an inflatable in-vivo capsule endoscope in an uninflated state into a cavity comprising liquid inside an organism, said capsule endoscope comprising a capsule-shaped body, an inflatable buoy external to the capsule-shaped body, and one or more image sensors for capturing in-vivo images housed interior to the capsule-shaped body;

activating an ex-vivo inflation device positioned outside of an organism when inflating the inflatable buoy positioned inside of the organism, wherein the ex-vivo inflation device is attached to the buoy by an elongated tether that traverses at least a portion of the gastro-intestinal (GI) tract of the organism, wherein the ex-vivo inflation device is activated to inflate the inflatable buoy by injecting an above threshold volume of gas into the inflatable buoy to reduce the specific gravity of the in-vivo capsule endoscope, such that, the inflatable in-vivo capsule endoscope floats in a liquid cavity of the GI tract;

releasing a connection between the elongated tether and the capsule-shaped body; and magnetically navigating the floating in-vivo capsule endoscope by exposing one or more permanent magnets housed interior to the capsule-shaped body having a permanent magnetic dipole moment to an externally generated magnetic field that magnetically guides the inflatable in-vivo capsule endoscope.

2. The method of 1 comprising causing the inflatable in-vivo capsule endoscope to float by injecting a volume of gas such that the density of the in-vivo capsule endoscope is less than or equal to the density of water.

3. The method of 1 comprising causing the inflatable in-vivo capsule endoscope to float by a combination of injecting a volume of gas and magnetically lifting the capsule by exposure to an externally generated magnetic field.

4. The method of 1 comprising deflating the inflatable buoy by expelling gas such that the inflatable in-vivo capsule endoscope sinks in the liquid.

5. The method of 1 comprising injecting or expelling gas to a desired volume or pressure to tune the floatation height level of the inflatable in-vivo capsule endoscope relative to the height level of the liquid.

6. The method of 1, wherein the inflation buoy has a corkscrew-shaped surface such that the inflatable capsule endoscope rotates in a spiral motion when it is magnetically navigated thorough a channel.

7. The method of 6 comprising magnetically rotating the in-vivo capsule endoscope about its longitudinal axis to propel the corkscrew-shaped surface.

8. The method of 1, wherein the inflation buoy is positioned asymmetrically relative to a radial axis of the capsule body, comprising orienting the capsule-shaped body by inflating the inflation buoy.

* * * * *